United States Patent [19]

Tseng et al.

[11] Patent Number: 5,126,340
[45] Date of Patent: * Jun. 30, 1992

[54] 4-[(SUBSTITUTED)ALKYLCARBONYL]-4,5-DIHYDRO AND 4,5,6,7-TETRAHYDRO-7-[(SUBSTITUTED)-PHENYL]PYRAZOLO[1,5-A]PYRIMIDINE-3-CARBONITRILES

[75] Inventors: Shin S. Tseng, Bridgewater, N.J.; Herbert J. Brabander, Nanuet; Joseph W. Epstein, Monroe, both of N.Y.

[73] Assignee: American Cyanamid Company, Stamford, Conn.

[*] Notice: The portion of the term of this patent subsequent to Oct. 16, 2007 has been disclaimed.

[21] Appl. No.: 565,766

[22] Filed: Aug. 10, 1990

Related U.S. Application Data

[60] Division of Ser. No. 238,005, Aug. 29, 1988, Pat. No. 4,963,553, which is a continuation-in-part of Ser. No. 919,731, Oct. 16, 1986, abandoned.

[51] Int. Cl.$^5$ .............. A61K 31/535; A61K 31/495; C07D 487/04
[52] U.S. Cl. ................ 514/233.2; 514/258; 544/117; 544/281
[58] Field of Search .............. 544/117, 281; 514/233.2, 258

[56] References Cited

U.S. PATENT DOCUMENTS 4,448,962 5/1984 Irikura et al. .............. 544/362
4,963,553 10/1990 Tseng et al. .............. 514/258

FOREIGN PATENT DOCUMENTS 264773 4/1988 European Pat. Off. .

*Primary Examiner*—Mukund J. Shah
*Assistant Examiner*—F. Bernhardt
*Attorney, Agent, or Firm*—H. G. Jackson

[57] ABSTRACT

Novel compounds of the formula

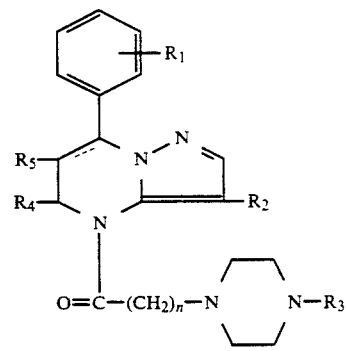

wherein n is an integer from 1 to 4 inclusive; $R_1$ represents a mono- or disubstituent of hydrogen, lower alkyl($C_1$-$C_3$), lower alkoxy ($C_1$-$C_3$), halogen, nitro or trifluoromethyl; $R_2$ is cyano, carboxamido, ethyl carboxylate or halogen; $R_3$ is hydrogen, straight or branched chain lower alkyl ($C_1$-$C_3$), alkenyl ($C_2$-$C_3$), alkynyl($C_2$-$C_3$), cycloalkyl($C_3$-$C_6$), hydroxyalkyl($C_1$-$C_3$), dimethylaminoalkyl($C_1$-$C_3$), ethylcarboxylate, alkyl($C_1$-$C_{13}$)carbonyl, 1-(methylethyl)acetamide, cyclohexylethyl, phenyl, mono- or disubstituted phenyl (wherein the phenyl substituent is halogen, trifluoromethyl, lower alkyl($C_1$-$C_3$) or lower alkoxy ($C_1$-$C_3$)), benzyl, mono- or disubstituted benzyl (wherein the benzyl substituent is halogen, lower alkyl($C_1$-$C_3$), lower alkoxy($C_1$-$C_3$) or trifluoromethyl), benzoyl, 4-methoxybenzoyl, straight or branched chain alkyl($C_2$-$C_3$)phenyl, 4-chlorophenylphenylmethyl, 1,3-benzodioxol-5-ylmethyl, 1,3-benzodioxol-5-yl, 2-furanylcarbonyl, 2-pyrimidinyl, 2-pyridinyl, 4-morpholinyl-2-oxoethyl, 1-pyrrolidinyl-2-oxoethyl, bis(4-fluorophenyl)methyl, phenylcarboxamido, mono- and disubstituted phenylcarboximido (wherein the phenyl substituents is halogen, trifluoromethyl or lower alkyl ($C_1$-$C_3$)), adamantanoyl, 3-phenoxypropyl, 5-chloro-2-methoxyphenylacetamide, (2-oxo-1-pyrrolidinyl)-2-butynyl, phenylmethylcarboxylate, or (2-phenyl-2H-1,2,3-triazol-4-yl)methyl; $R_4$ and $R_5$ are independently hydrogen or lower alkyl($C_1$-$C_3$); the dotted line between positions 6 and 7 of the pyrimidine ring represents the presence or absence of a double bond; and the pharmacologically acceptable salts thereof; methods of producing them; therapeutic compositions containing them; and methods of using them to treat anxiety, hypertension, depression, senile dementia, cognitive defects and other neural behavior problems in warmblooded animals.

10 Claims, No Drawings

4-[(SUBSTITUTED)ALKYLCARBONYL]-4,5-DIHYDRO AND -4,5,6,7-TETRAHYDRO-7-[(SUBSTITUTED)-PHENYL]PYRAZOLO[1,5-A]PYRIMIDINE-3-CARBONITRILES

This is a divisional of co-pending U.S. application Ser. No. 07/238,005, filed on Aug. 29, 1988, (now U.S. Pat. No. 4,963,553 (1990)), which in turn is a Continuation-in-part of U.S. Ser. No. 919,731 filed Oct. 16, 1986, now abandoned.

BRIEF SUMMARY OF THE INVENTION

The invention relates to new organic compounds and more particularly is concerned with novel 4-[(substituted)alkylcarbonyl]-4,5-dihydro- and -4,5,6,7-tetrahydro-7-[(substituted) phenyl]-pyrazolo]1,5-a]pyrimidine-3-carbonitriles, which have utility as anxiolytic agents, hypotensive agents, antidepressant agents and as agents for the treatment of senile dementia, cognitive and related neural behavioral problems in mammals. The compounds of the invention may be represented by the following structural formula:

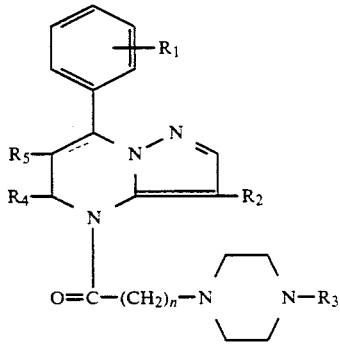

wherein n is an integer from 1 to 4 inclusive; $R_1$ represents a mono- or disubstituent of hydrogen, lower alkyl($C_1$–$C_3$), lower alkoxy($C_1$–$C_3$), halogen, nitro or trifluoromethyl; $R_2$ is cyano, carboxamido, ethyl carboxylate or halogen; $R_3$ is hydrogen, straight or branched chain lower alkyl($C_1$–$C_3$), alkenyl($C_2$–$C_3$), alkynyl($C_2$–$C_3$), cycloalkyl($C_3$–$C_6$), hydroxyalkyl($C_1$–$C_3$), dimethylaminoalkyl($C_1$–$C_3$), ethoxycarbonyl, alkyl($C_1$–$C_{13}$)carbonyl, 2-(methylethyl)amino-2-oxoethyl, cyclohexylethyl, phenyl, mono- or disubstituted phenyl (wherein the phenyl substituents are halogen, trifluoromethyl, lower alkyl($C_1$–$C_3$) or lower alkoxy($C_1$–$C_3$)), benzyl mono- or disubstituted benzyl (wherein the benzyl substituents are halogen, lower alkyl($C_1$–$C_3$), lower alkoxy($C_1$–$C_3$) or trifluoromethyl, benzoyl, 4-methoxybenzoyl, straight or branched chain alkyl($C_2$–$C_3$)phenyl, (4-chlorophenyl)-phenylmethyl, 1,3-benzodioxol-5-ylmethyl, 1,3-benzodioxol-5-yl, 2-furanylcarbonyl, 2-pyrimidinyl, 2-pyridinyl, 4-morpholinyl-2-oxoethyl, 1-pyrrolidinyl-2-oxoethyl, bis(4-fluorophenyl)methyl, phenylcarboxamido, mono- or disubstituted phenylcarboximido (wherein the phenyl substituents are halogen, trifluoromethyl or lower alkyl($C_1$–$C_3$)), adamantanoyl, 3-phenoxypropyl, [2-]]5-chloro-2-methoxyphenyl]amino]-2-oxoethyl], (2-oxo-1-pyrrolidinyl)-2-butynyl, phenylmethylcarboxylate, or (2-phenyl-2H-1,2,3-triazol-4-yl)methyl; $R_4$ and $R_5$ are independently hydrogen or lower alkyl($C_1$–$C_3$); the dotted line between positions 6 and 7 of the pyrimidine ring represents the presence or absence of a double bond; and the pharmacologically acceptable salts thereof.

The invention includes novel compositions of matter containing the above defined compounds which are useful as anxiolytic agents, hypotensive agents, antidepressant agents and as agents for the treatment of cognititive and related neural behavioral problems in mammals and the methods for treating anxiety, hypertension, depression and neural behavioral problems in mammals therewith.

The invention also includes the process for producing the novel compounds described hereinabove.

DETAILED DESCRIPTION OF THE INVENTION

The novel compounds of the invention are in general obtainable as white, yellow or tan crystalline solids having characteristic melting points and absorption spectra. They are appreciably soluble in many organic solvents such as lower alkanols, chloroform, dichloromethane, tetrahdyrofuran, acetone, N,N-dimethylformamide and the like, but are relatively insoluble in water. These compounds are organic bases and thus are capable of forming acid-addition salts with a variety of organic and inorganic salt-forming reagents. Thus, acid-addition salts, formed by admixture of the organic free base with an equivalent of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid addition salts of the novel compounds of the invention are, in general, crystalline and ethanol but relatively insoluble in non-polar organic solvents such as diethyl ether, benzene, toluene and the like. For purpose of this invention the free bases are equivalent to their non-toxic acid-addition salts.

The novel 4-[(substituted)alkylcarbonyl]-4,5-dihydro- and -4,5,6,7-tetrahydro-7-[(substituted)-phenyl]-pyrazolo[1,5a]pyrimidine-3-carbonitrile compounds of the present invention may be readily prepared as set forth in the following reaction scheme:

Scheme I

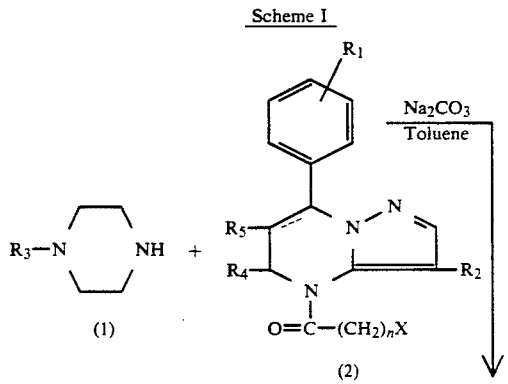

-continued
Scheme I

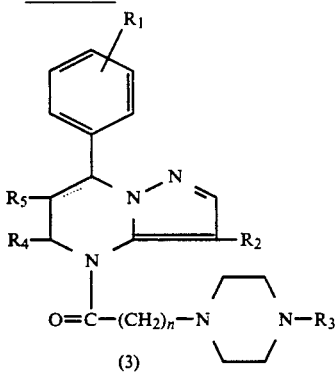

(3)

In accordance with Scheme I a piperazine (1) where $R_3$ is as described above is reacted with a halo-alkanoyl-4,5-dihydro- or -4,5,6,7-tetrahydro-7-substituted phenyl pyrazolo[1,5-]pyrimidine-3-carbonitrile (2) where n, $R_1'$ $R_2$, $R_4$ and $R_5$ are as described above, X is a halide such as chloro or iodo, and an alkaline carbonate in toluene at reflux giving the products (3).

The pharmacological activity of the compounds of the invention are demonstrated in the following tests.

A test used to assess antianxiety effects is the non-conditioned passive avoidance procedure described by J. R. Vogel, B. Beer and D. E. Clody, "A Simple and Reliable Conflict Procedure for Testing Antianxiety Agents", Psychopharmacologia, 21, 1–7 (1971). A conflict situation is induced in rats by a modification of this method.

Groups of S naive, Wistar strain male rats (Royalhart Farms, New Hampton, N.J.), weighing 200–400 g each, were deprived of water for 48 hours. The test compounds were administered in single or graded, oral doses, suspended in 2% starch with 5% polyethylene glycol in distilled water and one drop of polysorbate 80. Control animals received the vehicle alone. At 60 minutes each rate was placed in an individual clear plastic chamber. Tap water was available ad libitum from a nipple located in a black box off the main chamber. A 0.7 milliampere AC shocking current was established between the stainless steel grid floor and the tap. After 20 licks of non-shocked drinking, a 2 second shocking current was administered to the rat. This ratio of 20 licks of non-shocked drinking followed by a 2 second shock was continued for a total of 3 minutes. The number of shocks taken by each rat during the 3 minute interval was recorded and compared to a control group. The test compounds are considered active if the number of shocks received by the test group is significantly higher than the control group by the Mann-Whitney U test. That is, the test compounds are considered active if they result in the treated rat taking slightly more than double the number of shocks that the untreated rat will take. Results of this in vivo test on representative active compounds of the invention are given in Table I.

TABLE I

| Compound | Conflict Procedure in Rats | |
|---|---|---|
| | Dose (mg/kg) | Result (No. of shocks per 3 min.) |
| 4,5-Dihydro-4-[(4-methyl-1-piperazinyl)acetyl]-7-[3-(trifluoromethyl)phenyl]pyrazolo- | 25 | 17.4 |
| [1,5-a]pyrimidine-3-carbonitrile, dihydrochloride 4-[[4-(2-Cyclohexylethyl)-1-piperazinyl]acetyl]-4,5-dihydro-7-[3-(trifluoromethyl)phenyl]-pyrazolo[1,5-a]pyrimidine-3-carbonitrile | 25 | 18.0 |

Another test utilized for the determination of anxiolytic activity is the measurement of the ability of a test compound to inhibit the binding of tritiated benzodiazepines to brain-specific receptors of mammals. A modification of the method described by R. F. Squire, et al., Nature, 266 (21), 732 (April, 1977) and h. Mohler, et al., Science, 198, 849 (1977) was employed.

Male albino rate (Wistar strain, weighting 150–200 g each) were obtained from Royalhart Farms. $^3$H-Methyldiazepam (79.9 Ci/mmol) and $^3$H-methyl-flunitrazepam (84.3 Ci/mmol) were obtained from New England Nuclear. The test compounds were solubilized in dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 G for 20 minutes to produce a crude $P_2$-synaptososmal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$ C.) until time of use. Frozen $P_2$ preparations were thawed and resuspended in four times the original homogenizing volume at time of assay.

The binding assay consisted of 300 $\mu$l of the $P_2$-fraction suspension (0.2–04. mg protein), 100 $\mu$l of test drug and 100 $\mu$l of $^3$H-diazepam (1.5 nM, final concentration), or $^3$H-flunitrazepam (1.0 mM, final concentration) which was added to 1.5 ml of 50 mM Tris.HCl (pH 7.4). Non-specific binding controls and total binding controls received 100 $\mu$l of diazepam (3 $\mu$M final concentration) and 100 $\mu$l of deionized water, respectively, in place of the test compound. Incubation for 30 minutes proceeded in ice and was terminated by filtration, under vacuum, through glass fiber filters, The filters were washed twice with 5 ml of ice-cold 50 mM Tris.HCl (pH 7.4) and placed in scintillation vials. After drying at 50°–60° C. for 30 minutes, 10 ml of diluent was added and the radioactivity determined in a scintillation counter.

Inhibition of binding was calculated by the difference between total binding and binding in the presence of test compound, divided by the total binding, ×100. Physiological activity can be shown by a test compound that inhibits $^3$H-benzodiazepine binding by 12% or more. Such in vitro activity is biologically relevant when the test compound also demonstrates statistically significant anxiolytic activity through in vivo studies.

The results of this in vitro test on representative compounds of this invention are given in Table II.

TABLE II

Inhibition of the Binding of ³H-Benzodiazepine to Brain-Specific Receptors of Rats

| Compound | % Inhibition |
|---|---|
| 4,5-Dihydro-4-[(4-methyl-1-piperazinyl)acetyl]-7-[3-(trifluoromethyl)phenyl]pyrazolo[1,5-a]pyrimidine-3-carbonitrile | 41 |
| 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile | 17 |
| 4[[4-(3,4-Dichlorophenyl)-1-piperazinyl]acetyl]-4,5-dihydro-7-[3-(trifluoromethyl)phenyl]pyrazolo[1,5-a]pyrimidine-3-carbonitrile, hydrochloride | 12 |
| 4-[(Dihexylamino)acetyl]-4,5-dihydro-7-[3-(trifluoromethyl)phenyl]pyrazolo[1,5-a]pyrimidine-3-carbonitrile | 24 |
| 4,5-Dihydro-4-[[4-[2-(4-morpholinyl)-2-oxoethyl]-1-piperazinyl]acetyl]-7-[3-(trifluoromethyl)phenyl]pyrazolo[1,5-a]pyrimidine-3-carbonitrile | 41 |
| 4-[2-[3-Cyano-7-[3-(trifluoromethyl)phenyl]pyrazolo[1,5-a]pyrimidin-4(5H)-yl]-2-oxoethyl]-N-(1-methylethyl)-1-piperazineacetamide | 41 |
| 4,5-Dihydro-4-[[4-[2-oxo-2-(1-pyrrolidinyl)ethyl]-1-piperazinyl]acetyl]-7-[3-(trifluoromethyl)phenyl]pyrazolo[1,5-a]pyrimidine-3-carbonitrile | 33 |
| 4-[[4-(2-Cyclohexylethyl)-1-piperazinyl]acetyl]-4,5-dihydro-7-[3-trifluoromethyl)phenyl]pyrazolo[1,5-a]pyrimidine-3-carbonitrile, dihydrochloride | 14 |
| 4-[2-[3-Cyano-7-[3-(trifluoromethyl)phenyl]pyrazolo[1,5-a]pyrimidin-4(5H)-yl]-2-oxoethyl]-1-piperazinecarboxylic acid, ethyl ester | 45 |
| 4-[[4-(2-Furanylcarbonyl)-1-piperazinyl]acetyl]-4,5-dihydro-7-[(3-trifluoromethyl)phenyl]pyrazolo[1,5-a]pyrimidine-3-carbonitrile, hydrochloride | 12 |
| 4,5-Dihydro-4-(1-piperazinylacetyl)-7-[3-(trifluoromethyl)phenyl]pyrazolo[1,5-a]pyrimidine-3-carbonitrile | 25 |
| 4-[2-[3-Cyano-7-[3-(trifluoromethyl)phenyl]pyrazolo[1,5-a]pyrimidin-4(5H)-yl]-2-oxoethyl]-N-phenyl-1-piperazinecarboxamide | 24 |
| N-(5-Chloro-2-methoxyphenyl)-4-[2-[3-cyano-7-[3-(trifluoromethyl)phenyl]pyrazolo[1,5-a]pyrimidin-4(5H)-yl]-2-oxoethyl]-1-piperazineacetamide | 15 |
| 4,5,6,7-Tetrahydro-4-[[4-phenylmethyl-1-piperazinyl]acetyl]-7-[3-(trifluoromethyl)phenyl]pyrazolo[1,5-a]-pyrimidine-3-carbonitrile | 14 |
| 4,5,6,7-Tetrahydro-4-[[4-(phenylmethy)-1-piperazinyl]acetyl]-7-[3-(trifluoromethyl)phenyl]pyrazolo[1,5-a]pyrimidine-3-carbonitrile, dihydrochloride | 12 |

The novel compounds of the invention are active hypotensive agents at nontoxic doses when administered to mammals. These compounds were tested or hypotensive activity by the method of P. B. Chan and D. W. Poorvin, Clinical and Experimental Hypertension, (6), 817–830 (1979). Male, 16 week old, spontaneously hypertensive rats of the Okamoto strain (Taconic Farms, Germantown, N.Y.) having an average mean arterial blood pressure of 160±1.5 mm of mercury are used in the test. A rat is dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra.

The results of this test on representative compounds of the present invention appear below in Table III.

TABLE III

Reduction of Mean Arterial Blood Pressure in Spontaneously Hypertensive Rats

| Compound | MABP/mmHg |
|---|---|
| 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile | 120 |
| 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile, dihydrochloride | 137 |
| 4-[[4-[(4-Chlorophenyl)phenylmethyl]-1-piperazinyl]acetyl]-4,5-dihydro-7-[3-(trifluoromethyl)phenyl]pyrazolo[1,5-a]pyrimidine-3-carbonitrile | 134 |
| 4,5-Dihydro-4-[(4-phenyl-1-piperazinyl)acetyl]-7-[3-(trifluoromethyl)phenyl]pyrazolo[1,5-a]pyrimidine-3-carbonitrile | 137 |
| 4-[[4-(3-Chlorophenyl)-1-piperazinyl]acetyl]-4,5-dihydro-7-[3-(trifluoromethyl)phenyl]pyrazolo[1,5-a]pyrimidine-3-carbonitrile | 124 |
| 4,5-Dihydro-4-[[4-(2-pyrimidinyl)-1-piperazinyl]acetyl]-7-[3-(trifluoromethyl)phenyl]pyrazolo[1,5-a]pyrimidine-3-carbonitrile | 127 |
| 4-[[4-(4-Fluorophenyl)-1-piperazinyl]acetyl]-4,5-dihydro-7-[3-(trifluoromethyl)phenyl]pyrazolo[1,5-a]pyrimidine-3-carbonitrile | 130 |
| 4-[3-[4-[(4-Chlorophenyl)methyl]-1-piperazinyl]-1-oxopropyl]-4,5-dihydro-7-[3-(trifluoromethyl)phenyl]pyrazolo[1,5-a]pyrimidine-3-carbonitrile | 138 |
| 4,5-Dihydro-4-[[4-[2-(4-morpholinyl)-2-oxoethyl]-1-piperazinyl]acetyl]-7-[3-trifluoromethyl)phenyl]pyrazolo[1,5-a]pyrimidine-3-carbonitrile | 129 |
| 4-[2-[3-Cyano-7-[3-(trifluoromethyl)phenyl]pyrazolo[1,5-a]pyrimidin-4(5H)-yl]-2-oxoethyl]-N-(1-methylethyl)-1-piperazineacetamide | 129 |
| 4-[[4-[Bis(4-fluorophenyl)methyl]-1-piperazinyl]acetyl]-4,5-dihydro-7-[3-(trifluoromethyl)phenyl]pyrazolo[1,5-a]pyrimidine-3-carbonitrile | 121 |
| 4-[2-[3-Cyano-7-[3-(trifluoromethyl)phenyl]pyrazolo[1,5-a]pyrimidin-4(5H)-yl]-2-oxoethyl]-N-phenyl-1-piperazinecarboxamide | 125 |
| N-(5-Chloro-2-methoxyphenyl)-4-[2-[3-cyano-7-[3-(trifluoromethyl)phenyl]pyrazolo[1,5-a]pyrimidin-4(5H)-yl]-2-oxoethyl]-1-piperazineacetamide | 139 |
| 4,5-Dihydro-4-[[4-(2-propenyl)-1-piperazinyl]acetyl]-7-[3-(trifluoromethyl)phenyl]pyrazolo[1,5-a]pyrimidine-3-carbonitrile | 139 |
| 4-[(4-Cyclobutyl-1-piperazinyl)acetyl]-4,5-dihydro-7-[3-(trifluoromethyl)phenyl]pyrazolo[1,5-a]pyrimidine-3-carbonitrile | 124 |
| 4,5-Dihydro-4-[[4-(1-methylethyl)-1-piperazinyl]acetyl]-7-[3-(trifluoromethyl)phenyl]pyrazolo[1,5-a]pyrimidine-3-carbonitrile | 139 |

The novel compounds of the invention possess the ability to enhance neutral function in warm blooded animals affected by behavioral neurological problems, including the cognitive deterioration associated with decreased neutral function which occurs with cerebral insufficiency, aging, dementia, and similar conditions.

A useful in vivo test associated with decreased neural function in mammals is the Passive Avoidance Anoxic Induced Amnesia Test. This test is used to determine the attenuation of anoxic induced amnesia in mice treated with drug, as compared to saline treated control animals with no drug.

A shock-motivated, single trial, step-through passive avoidance procedure is used. Groups of 25 Swiss-Webster, middle-aged mice (9 months of age) are placed singly in the front chamber of a 2-chamber box and are allowed to voluntarily cross into the rear chamber. As soon as the mouse enters the rear chamber, a door automatically traps the animal and a mild electric shock (0.4 mA for 4 seconds) is delivered to its feet. Following the foot shock, the mice are initially placed in an anoxic environment (0% oxygen) for 12 seconds, which quickly induces unconsciousness. They are then placed in an hypoxic environment (15% oxygen) for four minutes which prolongs the oxygen deprived state, maintaining unconsciousness. All testing is performed 24 hours later, and in all cases the mice appear fully recovered from the previous anoxic/hypoxic treatment. All test compounds are administered intraperitoneally at a dose of 10–200 mg/kg, 30 minutes prior to training and testing. Control animals are injected intraperitoneally only with saline at 0.01 ml/g of body weight.

The latent period prior to entering the rear chamber is recorded for both training and testing sessions. The greater the memory of being shocked, the greater the reluctance to enter into the rear chamber and the higher will be the latent period prior to re-entry. An improvement (lengthened latency) of 30% over saline control scores is considered active. The result of this test appear in Table IV.

TABLE IV

Passive Avoidance Anoxic Induced Amnesia Test

| Compound | Dose (mg/kg) | % Improvement |
|---|---|---|
| 4,5-Dihydro-4-[[4-(phenylmethyl)-1-piperazinyl]acetyl]-7-[3-(trifluoromethyl)phenyl]pyrazolo-[1,5-a]pyrimidine-3-carbonitrile | 100<br>200 | 65<br>93 |
| 4,5-Dihydro-4-[[4-[4-(2-oxo-1-pyrrolidinyl)-2-butynyl]-1-piperazinyl]acetyl]-7-[3-(trifluoromethyl)phenyl]pyrazolo[1,5-a]pyrimidine-3-carbonitrile | 1 | 63 |
| 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile, monohydrochloride | 10 | 30 |
| 7-(4-Chlorophenyl)-4-[[4-[(3-chlorophenyl)methyl]-1-piperazinyl]acetyl]-4,5-dihydro-6-methylpyrazolo-[1,5-a]pyrimidine-3-carbonitrile, dihydrochloride | 10 | 66 |
| 4,5-Dihydro-4-[[4-(2-phenyl-2H-1,2,3-triazol-4-yl)methyl]-1-piperazinyl]acetyl]-7-[3-(trifluoromethyl)phenyl]pyrazolo[1,5-a]pyrimidine-3-carbonitrile | 100 | 92 |
| 4,5-Dihydro-7-phenyl-4-[[4-(phenylmethyl)-1-piperazinyl]acetyl]pyrazolo[1,5-a]pyrimidine-3-carbonitrile | 25 | 45 |
| 4,5-Dihydro-4-[[4-(1-phenylethyl)-piperazinyl]acetyl]-7-[3-(trifluoromethyl)phenyl]pyrazolo[1,5-a]pyrimidine-3-carbonitrile | 25 | 39 |

The compounds of the invention are useful as antidepressant agents in warm-blooded animals as verified in the following tests. First, the antidepressant properties of these compounds were tested by measuring their ability to counteract depression induced in animals by the administration of tetrabenazine methanesulfonate. Each test compound was administered orally to 10 mice at a dose of 25 mg/kg of body weight. Thirty minutes later, tetrabenazine methane sulfonate was administered intraperitoneally to each mouse at a dose of 39 mg/kg of body weight, which dose is known to depress markedly the exploratory behavior of normal mice. Thirty minutes later the mice were tested for their exploratory behavior as described by E. Greenblatt and A. C. Osterberg, Toxicology and Applied Pharmacology, 7. 566–578 (1965). A compound is considered active if 3 or more of 10 mice are protected against the tetrabenazine-induced effects.

The results of this test on representative compounds of this invention appear in Table V.

TABLE V

| Tetrabenazine-Induced Depression | |
|---|---|
| Compound | Result |
| 4,5-Dihydro-4-[[4-(phenylmethyl)-1-piperazinyl]-acetyl]-7-[3-(trifluoromethyl)phenyl]pyrazolo-[1,5-a]pyrimidine-3-carbonitrile | Active |
| 4,5-Dihydro-4-[[4-[(3-methoxyphenyl)methyl]-1-piperazinyl]acetyl]-7-[3-(trifluoromethyl)phenyl]-pyrazolo[1,5-a]pyrimidine-3-carbonitrile | Active |
| 4,5-Dihydro-4-[[4-[(3-methoxyphenyl)methyl]-1-piperazinyl]acetyl]-7-[3-(trifluoromethyl)phenyl]-pyrazolo[1,5-a]pyrimidine-3-carbonitrile, dihydrochloride | Active |
| 4-[[4-(1,3-Benzodioxol-5-ylmethyl)-1-piperazinyl]-acetyl]-4,5-dihydro-7-[3-(trifluoromethyl)-phenyl]pyrazolo[1,5-a]pyrimidine-3-carbonitrile | Active |

This activity of the compounds of the invention as antidepressant agents was further verified# in the following test which measures the ability of a test compound to inhibit 3H-imipramine binding to human platelet membranes.

Platelet membranes were obtained using the procedure described by Wennogle, L. et. al., Pharmac. Biochem. Behav., 15. 975 (1981). Fresh human platelet concentrates (less than 48 hours old) were obtained from the New York Blood Center. These concentrates were prepared in a citrate-dextrose anticoagulant using standard techniques. Platelets were washed twice by centrifugation (2500×G, 10 minutes) in 50 volumes of an antiprotease buffer containing 0.005M Tris potassium chloride, 0.12M sodium chloride, 0.05M Tris pH 7.5, 0.025 Units/ml aprotinin, 0.05 µg/m pepstatin, $2 \times 10^{-5}$ bacitracin, 3 mM ethylenediaminetetraacetic acid and 1.0 mM ethyleneglycol-bis (β-aminoethylether)N,N'-tetraacetic acid. Antiproteases have been shown to inhibit the breakdown of the 3H-imipramine receptor [Wennogle, L. et al. (vide supra)]. All procedures were conducted at 0° C. using plastic laboratory-ware throughout the platelet membrane preparation. Platelets were resuspended in 20 volumes of buffer and sonicated 3 times using 10 second bursts of a Branson sonifier (cell disrupter 350) at setting 6 (standard ¾ inch horn), keeping the sample on ice throughout the procedure. Platelet membranes were then washed twice at 18,000×G for 20 minutes with 50 volumes of the antiprotease buffer and resuspended to 3.0 mg. protein/ml using the Bradford protein analysis with bovine gamma globulin as standard. Membranes were used immediately or stored frozen in liquid nitrogen.

The displacement of 3H-imipramine binding to human platelet membranes was performed essentially as described by Paul, S. M., et al., Life Sci., 953 (1980) with the following modifications. Membranes (0.3 mg protein) were suspended in antiprotease buffer with both 3.0 mM 3H-imipramine (New England Nuclear) and displacing drug or buffer in a total volume of 250 #1 in glass test tubes. Samples were incubated for 90 minutes at 0° C., then diluted to 5 ml in 0.12M sodium chloride, 0.005M potassium chloride, 0.05M Tris pH 7.5

(wash buffer) and immediately filtered through GF/B Whatman Filters and washed twice with 5 ml of wash buffer. Filters were counted in a liquid scintillation counter after addition of Beckman HP Scintillant.

Non-specific binding of 3H-imipramine was defined as that fraction (generally 35%) of radioactivity that was not displaced by 10 µM desmethylimipramine. Specific binding was determined by subtraction of this non-specific level from values for total 3H-imipramine binding which were measured by incubating 3H-imipramine in the absence of displacing drug. Compounds were tested in duplicate test tubes at a concentration of 10 µM. Compounds which inhibited binding by more than 50% were considered to be active.

The results of this test on representative compounds of this invention appear in Table VI.

TABLE VI

| 3H-Imipramine Binding to Human Platelet Membranes | |
|---|---|
| Compound | % Inhibition |
| 4,5-Dihydro-4-[[4-[(3-methoxyphenyl)methyl]-1-piperazinyl]acetyl]-7-[3-(trifluoromethyl)phenyl]pyrazolo[1,5-a]pyrimidine-3-carbonitrile | 78 |
| 4-[[4-(1,3-Benzodioxol-5-ylmethyl)-1-piperazinyl]acetyl]-4,5-dihydro-7-[3-(trifluoromethyl)phenyl]pyrazolo[1,5-a]pyrimidine-3-carbonitrile | 81 |
| 4-[[4-[2-(Dimethylamino)ethyl]-1-piperazinyl]acetyl]-4,5-dihydro-7-[3-(trifluoromethyl)phenyl]pyrazolo[1,5-a]pyrimidine-3-carbonitrile, dihydrochloride | 72 |
| 4-[[4-[3-(Dimethylamino)propyl]-1-piperazinyl]acetyl]-4,5-dihydro-7-[3-(trifluoromethyl)phenyl]pyrazolo[1,5-a]pyrimidine-3-carbonitrile | 89 |
| 4-[3-[4-[(4-Chlorophenyl)methyl]-1-piperazinyl]-1-oxopropyl]-4,5-dihydro-7-[3-trifluoromethyl)phenyl]pyrazolo[1,5-a]pyrimidine-3-carbonitrile, dihydrochloride | 85 |
| 4-[[4-[(4-Chlorophenyl)methyl]-1-piperazinyl]acetyl]-7-[3-(trifluoromethyl)phenyl]pyrazolo[1,5-a]pyrimidine-3-carbonitrile | 84 |
| 4,5-Dihydro-4-[1-oxo-3-[4-(phenylmethyl)-1-piperazinyl]propyl]-7-[3-(trifluoromethyl)phenyl]pyrazolo[1,5-a]pyrimidine-3-carbonitrile | 80 |
| 4,5,6,7-Tetrahydro-4-[[4-(3-phenoxypropyl)-1-piperazinyl]acetyl]-7-[3-(trifluoromethyl)phenyl]pyrazolo[1,5-a]pyrimidine-3-carbonitrile | 57 |
| 7-(2,5-Dichlorophenyl)-4,5-dihydro-4-[1-oxo-3-[4-(phenylmethyl)-1-piperazinyl]propyl]pyrazolo[1,5-a]pyrimidine-3-carbonitrile | 79 |

The hypoxic survival test is a useful in vivo test for measuring the effectiveness of central nervous system-acting drugs in enhancing survival in an hypoxic environment relative to the known parasympathomimetic agent physostigmine. This assay shows the enhanced survival of animals in an hypoxic environment after treatment with drug as compared to saline-treated control animals.

Extensive testing has demonstrated that under conditions of 10% oxygen, only 5-20% of control mice survive after 5 minutes, whereas 60-80% of the physostigmine-treated mice survive. Drugs are tested by intraperitoneal injection of groups of mice 30 minutes prior to placing them in an hypoxic environment and measuring survival. The rationale of this test is that drugs which enhance survival under hypoxic conditions without concomitant depression or sedative side effects, do so by enhancing brain metabolism, i.e., by improving energy supply relative to demand and so preserving normal brain function under conditions of reduced energy metabolism. Considering the dependence of the brain on a constant supply of energy, drugs which have this property may have many far-reaching therapeutic indications, including aiding recovery from stroke and closed head injury and reducing the deleterious effects of age-related central nervous system deficits. For example, deficiencies in energy metabolism are thought to contribute significantly to the neurochemical and neurophysiological dysfunctions of aging and senile dementia.

In the hypoxic survival test, groups of 20 Royal Hart mice (6weeks of age) were injected intraperitoneally with a test compound in saline at various doses ranging from 1 to 200 mg/kg, 30 minutes prior to placing them in an hypoxic mixture (10% oxygen, 90% carbon dioxide) and measuring survival after 5 minutes.

A control group of 20 mice was injected intraperitoneally with saline (0.01 ml/g of body weight) and processed as described above.

Another group of 20 mice was injected intraperitoneally with 0.125 mg/kg of physostigmine in saline and processed as described above.

Results of this test on representative compounds of this invention appear in Table VII.

TABLE VII

| Hypoxic Survival Test | | |
|---|---|---|
| Compound | Dose (mg/kg) | % Survivors |
| 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile | 10<br>100 | 40<br>48 |
| 7-(4-Chlorophenyl)-4,5-dihydro-4-[[4-(phenylmethyl)-1-piperazinyl]acetyl]pyrazolo[1,5-a]pyrimidine-3-carbonitrile | 10<br>100 | 50<br>82.5 |
| 7-(4-Chlorophenyl)-4,5-dihydro-4-[[4-[2-(trifluoromethyl)phenyl]methyl]-1-piperazinyl]acetyl]pyrazolo[1,5-a]pyrimidine-3-carbonitrile | 10<br>100 | 55<br>90 |
| 7-(2,5-Dichlorophenyl)-4-[[4-(2,5-dimethylphenyl)-1-piperazinyl]-acetyl]-4,5-dihydropyrazolo[1,5-a]pyrimidine-3-carbonitrile | 100<br>200 | 45<br>80 |
| 4,5-Dihydro-4-[[4-[4-(2-oxo-1-pyrrolidinyl)-2-butynyl]-1-piperazinyl]acetyl]-7-[3-(trifluoromethyl)phenyl]pyrazolo[1,5-a]pyrimidine-3-carbonitrile | 100 | 68 |
| 4,5-Dihydro-5-methyl-4[[4-(phenylmethyl)-1-piperazinyl]-acetyl]-7-[3(trifluoromethyl)-phenyl]pyrazolo[1,5-a]pyrimidine-3-carbonitrile dihydrochloride | 100 | 43 |
| 4,5-Dihydro-6-methyl-4[[4-(phenylmethyl)-1-piperazinyl]-acetyl]-7-[3-(trifluoromethyl)-phenyl]pyrazolo[1,5-a]pyrimidine-3-carbonitrile, dihydrochloride | 100 | 73 |
| 4,5,6,7-Tetrahydro-4-[[4-(phenylmethyl)-1-piperazinyl]acetyl]-7-[3-(trifluoromethyl)phenyl]pyrazolo[1,5-a]pyrimidine-3-carbonitrile | 100 | 80 |
| 4,5-Dihydro-4-[[4-(phenylmethyl)-1-piperazinyl]acetyl]-7-[3- | 100 | 83 |

TABLE VII-continued

Hypoxic Survival Test

| Compound | Dose (mg/kg) | % Survivors |
|---|---|---|
| (trifluoromethyl)phenyl]pyrazolo[1,5-a]pyrimidine-3-carbonitrile, hydrochloride | | |
| 4,5-Dihydro-4-[[4-(3-trifluoromethylphenyl)methyl]-1-piperazinyl]acetyl]-7-[3-(trifluoromethyl)phenyl]pyrazolo[1,5-a]pyrimidine-3-carbonitrile | 100 | 40 |
| 4,5-Dihydro-4-[[4-(3-trifluoromethyl-phenyl)methyl]-1-piperazinyl]acetyl]-7-[3-(trifluoromethyl)phenyl]pyrazolo[1,5-a]pyrimidine-3-carbonitrile, dihydrochloride | 100 | 85 |
| 7-(3-Chlorophenyl)-4-[[4-[(3-chlorophenyl)methyl-1-piperazinyl]acetyl]-4,5-dihydro-6-methyl-pyrazolo[1,5-a]pyrimidine-3-carbonitrile, dihydrochloride | 100<br>50 | 77<br>73 |
| 7-(4-Chlorophenyl)-4-[[4-[(3-chlorophenyl)methyl]-1-piperazinyl]acetyl]-4,5-dihydro-6-methylpyrazolo[1,5-a]pyrimidine-3-carbonitrile, dihydrochloride | 200<br>100 | 73<br>62 |
| 7-(3-Chlorophenyl)-4,5-dihydro-6-methyl-4-[[4-[[3-(trifluoromethyl)phenyl]methyl]-1-piperazinyl]acetyl]pyrazolo[1,5-a]pyrimidine-3-carbonitrile | 200 | 73 |
| 4-[(4-Benzoyl-1-piperazinyl)acetyl]-4,5-dihydro-7-[3-(trifluoromethyl)phenyl]pyrazolo[1,5-a]pyrimidine-3-carbonitrile | 100 | 95 |
| 4,5-Dihydro-4-[[4-(2-phenylethyl)-1-piperazinyl]acetyl]-7-[3-(trifluoromethyl)phenyl]pyrazolo[1,5-a]pyrimidine-3-carbonitrile, dihydrochloride | 100 | 60 |
| 4-[[4-[Bis(4-fluorophenyl)methyl]-1-piperazinyl]acetyl]-4,5-dihydro-7-[3-(trifluoromethyl)phenyl]pyrazolo[1,5-a]pyrimidine-3-carbonitrile, dihydrochloride | 100 | 55 |
| 7-(2,5-Dichlorophenyl)-4,5-dihydro-4-[(4-phenyl-1-piperazinyl)acetyl]pyrazolo[1,5-a]pyrimidine-3-carbonitrile | 100 | 70 |
| 7-(2,5-Dichlorophenyl)-4,5-dihydro-4-[[4-(phenylmethyl)-1-piperazinyl]acetyl]pyrazolo[1,5-a]pyrimidine-3-carbonitrile | 100 | 50 |
| 4-[(4-Cyclobutyl-1-piperazinyl)acetyl]-4,5-dihydro-7-[3-(trifluoromethyl)phenyl]pyrazolo[1,5-a]pyrimidine-3-carbonitrile, dihydrochloride | 10 | 55 |
| 4-[[4-[(3-Chlorophenyl)methyl]-1-piperazinyl]acetyl]-4,5,6,7-tetrahydro-7-[3-(trifluoromethyl)phenyl]pyrazolo[1,5-a]pyrimidine-3-carbonitrile | 100 | 15 |
| 4-[[4-[(2,6-Dichlorophenyl)methyl]-1-piperazinyl]acetyl]-4,5,6,7-tetrahydro-7-[3-(trifluoromethyl)phenyl]pyrazolo[1,5-a]pyrimidine-3-carbonitrile | 10 | 25 |
| N-[4-Chloro-3-(trifluoromethyl)phenyl]-4-[2-[3-cyano-7-[3-(trifluoromethyl)phenyl]pyrazolo[1,5-a]pyrimidin-4(5H)-yl]-2-oxoethyl-1-piperazinecarboxamide | 100 | 15 |
| 4,5,6,7-Tetrahydro-4-[[4-(3-phenoxypropyl)-1-piperazinyl]acetyl]-7-[3-(trifluoromethyl)phenyl]pyrazolo[1,5-a]pyrimidine-3-carbonitrile | 10 | 15 |
| 4-[2-[3-Cyano-7-[3-(trifluoromethyl)phenyl]pyrazolo[1,5-a]pyrimidin-4(5H)-yl]-2-oxoethyl]-N-(2,4-difluorophenyl)-1-piperazinecarboxamide | 100 | 20 |
| 4,5-Dihydro-5-methyl-4-[[4-(phenylmethyl)-1-piperazinyl]acetyl]-7-[3-(trifluoromethyl)phenyl]pyrazolo[1,5-a]pyrimidine-3-carbonitrile | 100 | 25 |
| 7-(3-Chlorophenyl)-4,5-dihydro-6-methyl-4-[[4-(phenylmethyl)-1-piperazinyl]acetyl]pyrazolo[1,5-a]pyrimidine-3-carbonitrile, dihydrochloride | 100 | 30 |
| 7-(4-Chlorophenyl)-4,5-dihydro-6-methyl-4-[[4-(phenylmethyl)-1-piperazinyl]acetyl]pyrazolo[1,5-a]pyrimidine-3-carbonitrile, dihydrochloride | 100 | 25 |
| 4,5-Dihydro-4-[[4-(2-phenylethyl)-1-piperazinyl]acetyl]-7-[3-trifluoromethyl)phenyl]pyrazolo[1,5-a]pyrimidine-3-carbonitrile | 100 | 90 |
| 7-(4-Chlorophenyl)-4,5-dihydro-6-methyl-4-[[4-[[3-(trifluoromethyl)phenyl]methyl]-1-piperazinyl]acetyl]-pyrazolo[1,5-a]pyrimidine-3-carbonitrile, dihydrochloride | 200 | 37.5 |
| 7-(3-Chlorophenyl)-4,5-dihydro-6-methyl-4-[[4-[[3-(trifluoromethyl)phenyl]methyl]-1-piperazinyl]acetyl]-pyrazolo[1,5-a]pyrimidine-3-carbonitrile, sesquihydrochloride | 100 | 35 |
| 7-(3-Chlorophenyl)-4,5-dihydro-4-[[4-[(3-methoxyphenyl)methyl]-1-piperazinyl]acetyl]-6-methylpyrazolo[1,5-a]pyrimidine-3-carbonitrile, dihydrochloride | 100 | 65 |
| 4,5-Dihydro-4-[[4-(phenylmethyl)-1-piperazinyl]acetyl]-7-[3-(trifluoromethyl)phenyl]pyrazolo[1,5-a]pyrimidine-3-carboxamide | 10 | 15 |
| 4,5-Dihydro-4-[[4-[(2-phenyl-2H-1,2,3-triazol-4-yl)methyl]-1-piperazinyl]acetyl]-7-[3-(trifluoromethyl)phenyl]pyrazolo[1,5-a]pyrimidine-3-carbonitrile | 100 | 52.5 |
| 4,5-Dihydro-7-phenyl-4-[[4-(phenylmethyl)-1-piperazinyl]acetyl]pyrazolo[1,5-a]pyrimidine-3-carbonitrile | 100 | 50 |
| 4,5-Dihydro-4-[[4-[(3-methoxyphenyl)methyl]-1-piperazinyl]acetyl]-7-phenylpyrazolo[1,5-a]pyrimidine-3-carbonitrile | 100 | 55 |
| 4,5-Dihydro-4-[[4-[(3-methoxyphenyl)methyl]-1-piperazinyl]acetyl]-7-phenylpyrazolo[1,5-a]pyrimidine-3-carbonitrile, dihydrochloride | 10 | 45 |
| 3-Bromo-4,5-dihydro-4-[[4-(phenylmethyl)-1-piperazinyl]acetyl]-7-[3-(trifluoromethyl)phenyl]9 pyrazolo[1,5-a]pyrimidine | 100 | 35 |
| 4,5-Dihydro-7-[3-(trifluoromethyl)phenyl]-4-[[4-[[2-(trifluoromethyl)phenyl]methyl]-1-piperazinyl]acetyl]pyrazolo[1,5-a]pyrimidine-3-carbonitrile | 100 | 20 |
| 4,5-Dihydro-7-[3-(trifluoromethyl)phenyl]-4-[[4-[[2-(trifluoromethyl)phenyl]methyl]-1-piperazinyl]acetyl]pyrazolo[1,5-a]pyrimidine-3-carbonitrile, dihydrochloride | 10 | 30 |

TABLE VII-continued

Hypoxic Survial Test

| Compound | Dose (mg/kg) | % Survivors |
| --- | --- | --- |
| 4-[[4-(4-Fluorophenyl)-1-piperazinyl]acetyl]4,5-dihydro-7-[3-(trifluoromethyl)phenyl]pyrazolo[1,5-a]-pyrimidine-3-carbonitrile, monohydrochloride | 100 | 35 |
| 3-Bromo-4,5-dihydro-4-[[4-(phenylmethyl)-1-piperazinyl]acetyl]-7-[3-(trifluoromethyl)phenyl]pyrazolo-[1,5-a]pyrimidine, dihydrochloride | 10 | 20 |
| 3-Chloro-4,5-dihydro-4-[[4-(phenylmethyl)-1-piperazinyl]acetyl]-7-[3-(trifluoromethyl)phenyl]pyrazolo-[1,5-a]pyrimidine, dihydrochloride | 100 | 25 |
| 4-[[4-[(2-Fluorophenyl)methyl]-1-piperazinyl]acetyl]-4,5-dihydro-7-[3-(trifluoromethyl)phenyl]pyrazolo-[1,5-a]pyrimidine-3-carbonitrile | 100 | 55 |
| 7-(3-Chlorophenyl)-4-[[4-[(2-fluorophenyl)methyl]-1-piperazinyl]acetyl]-4,5-dihydro-6-methylpyrazolo[1,5-a]-pyrimidine-3-carbonitrile, dihydrochloride | 100 | 45 |
| 4-[2-[3-Cyano-7-[3-(trifluoromethyl)-phenyl]pyrazolo[1,5-a]pyrimidin-4(5H)-yl]-2-oxoethyl]-1-piperazinecarboxylic acid, phenylmethyl ester | 100 | 55 |
| 6-Ethyl-4,5-dihydro-4-[[4-(phenylmethyl)-1-piperazinyl]acetyl]-7-[3-(trifluoromethyl)phenyl]pyrazolo-[1,5-a]pyrimidine-3-carbonitrile, dihydrochloride | 200 | 42 |
| 4,5-Dihydro-6-methyl-7-[3-(trifluoromethyl)phenyl]-4-[[4-[[3-(trifluoromethyl)phenyl]methyl]-1-piperazinyl]-acetyl]pyrazolo[1,5-a]pyrimidine-3-carbonitrile, dihydrochloride | 100 | 40 |
| 6-Ethyl-4,5-dihydro-4-[[4-(phenylmethyl)-1-piperazinyl]acetyl]-7-[3-(trifluoromethyl)phenyl]pyrazolo-[1,5-a]pyrimidine-3-carbonitrile | 100 | 25 |
| 4,5-Dihydro-4-[[4-(4-methoxybenzoyl)-1-piperazinyl]acetyl]-7-[3-(trifluoromethyl)phenyl]pyrazolo[1,5-a]-pyrimidine-3-carbonitrile | 100 | 45 |
| 4,5-Dihydro-4-[[4-(4-methoxybenzoyl)-1-piperazinyl]acetyl]-7-[3-(trifluoromethyl)phenyl]pyrazolo[1,5-a]-pyrimidine-3-carbonitrile, monohydrochloride | 100 | 25 |
| 4,5-Dihydro-4-[[4-(1-phenylethyl)-1-piperazinyl]acetyl]-7-[3-(trifluoromethyl)phenyl]pyrazolo[1,5-a]pyrimidine-3-carbonitrile | 25 | 45 |
| 4,5-Dihydro-7-(3-methylphenyl)-4-[[4-(phenylmethyl)-1-piperazinyl]-acetyl]pyrazolo[1,5-a]pyrimidine-3-carbonitrile, dihydrochloride | 100 | 55 |

Compounds of the invention are administered in amounts ranging from about 0.1 mg to about 35.0 mg/kg of body weight per day for the treatment of depression and/or for the alleviation of anxiety in warm-blooded animals. A preferred dosage regimen for optimum results would be from about 0.5 mg to about 20.0 mg/kg of body weight per day and such dosage units are employed that a total of from about 35 mg to about 1.4 g of the active compound for a subject of about 70 kg of body weight are administered in a 24 hour period.

The novel compounds of the invention have been found to be highly useful for lowering elevated blood pressure in mammals when administered in amounts ranging from about 25 mg to about 100 mg/kg of body weight per day. A preferred dosage regimen for optimum results would be from about 10 mg to about 100 mg per dose. Such dosage units are employed that a total f from about 40 mg to about 400 mg of the active compound for a subject of about 70 kg of body weight are administered in a 24 hour period.

The compounds of the invention have been found to be useful as agents for the treatment of cognitive and related neural behavioral problems in mammals when administered in amounts ranging from about 5 mg to about 200 mg/kg of body weight per day. A preferred dosage regimen for optimum results would be from about 10 mg to about 50 mg/kg of body weight per day and such dosage units are employed that a total of from about 700 mg to about 3.5 mg of the active compound for a subject of about 70 kg of body weight are administered in a 24 hour period.

The dosage regimen for the above-described utilities may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The compounds may be orally administered, for example, with an inert diluent or with an assimilable edible carrier. They may be enclosed in hard or soft shell gelatin capsules or compressed into tablets. They may also be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

The compounds may also be administered parenterally or intraperitoneally. Solutions or suspensions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples.

EXAMPLE 1

4-(Chloroacetyl)-4,5-dihydro-7-[3-(trifluoromethyl)-phenyl]pyrazolo[1,5-a]pyrimidine-3-carbonitrile An 8.2 g portion of sodium cyanoborohydride was added portionwise to a solution of 20 g of 7-[3-(trifluoromethyl)phenyl]pyrazolo[1,5-a]pyrimidine-3-carbonitrile (U.S. Pat. No. 4,178,449) in 400 ml of acetic acid at ice bath temperature with stirring under nitrogen. The reaction was stirred at ice bath temperature for 45 minutes, then at room temperature for 3 hours, 1.7 g of sodium cyanoborohydride was added and stirring was continued for 2 more hours.

The precipitate was collected, washed with water and saved.

The acetic acid solution was concentrated to ½ volume and diluted with 250 ml of water. The resulting precipitate was collected, washed twice with water, combined with the above precipitate and dissolved in 600 ml of dichloromethane. This solution was washed twice with saturated aqueous sodium bicarbonate, dried, filtered and concentrated to a pale yellow solid. This solid was recrystallized from hot isopropanol, giving 14.8 g of 4,5-dihydro-7-[3-(trifluoromethyl)-phenyl]pyrazolo[1,5-a]pyrimidine-3-carbonitrile.

A mixture of 2.9 g of the above compound and 3.4 g of chloroacetic anhydride in 100 ml of toluene was heated with stirring at reflux for 5 hours. The reaction was cooled, 1 g of chloroacetic anhydride was added, the mixture was stirred 48 hours at room temperature, then refluxed for 5 hours and allowed to stand overnight at room temperature. The mixture was then concentrated in vacuo on a steam bath. The residue was slurried in ether and the white crystals collected, washed with ether and dried, giving 1.1 g of the desired intermediate, mp 179°–181° C.

EXAMPLE 2

4-(3-Chloro-1-oxopropyl-4,5-dihydro-7-[3-(trifluoromethyl)phenyl[pyrazolo]1,5-a] pyrimidine-3-carbonitrile To a stirred mixture of 4.5 g of 4,5-dihydro-7-[3-trifluoromethyl)phenyl]pyrazolo[1,5-a]-pyrimidine-3-carbonitrile and 3.6 g of [1,8-bis(dimethylamino) naphthalene, N,N,N',N',-tetramethyl-1,8-naphthalenediamine] in 120 ml of dry tetrahydrofuran, under nitrogen, was added dropwise, a solution of 3.9 g of 3-chloropropionyl chloride in 30 ml of tetrahydrofuran. The mixture was stirred for one hour, heated at reflux for 4 hours, then allowed to stand overnight. The mixture was filtered and the filtrate evaporated in vacuo on a steam bath. The residue was triturated with ether, filtered, washed with ether, dried and the solid was then heated to solution in 25 ml of acetonitrile and filtered. Refrigeration produced a solid which was collected, washed with ether and dried, giving 3 g of the desired produce, mp 183°–185° C.

EXAMPLE 3

4-(Chloroacetyl)-7-(3-chlorophenyl)-4,5-dihydropyrazolo[1,5-a]pyrimidine-3-carbonitrile A 23.4 g portion of 7-(3-chlorophenyl)-pyrazolo[1,5-a]pyrimidine-3-carbonitrile and 11.7 g of sodium cyanoborohydride in 500 ml of acetic acid were reacted as described in Example 1, giving 18.4 g of 4,5-dihydro-7-(3-chlorophenyl)pyrazolo[1,[1,5-a]-pyrimidine-3-carbonitrile.

An 18.1 g portion of the above compound and 15 g of chloroacetic anhydride in 200 ml of toluene, were reacted as described in Example 1, giving 15 g of the desired intermediate, mp 196°–198° C.

EXAMPLE 4

4,5-Dihydro-4-(iodoacetyl)-7-[3-(trifluoromethyl)-phenyl]pyrazolo[1,5-a]pyrimidine-3-carbonitrile A mixture of 1.8 g of 4-(chloroacetyl)4,5-dihydro-[3-(trifluoromethyl)phenyl]pyrazolo[1,5-a]-pyrimidine-3-carbonitrile and 825 mg of sodium iodide in 25 ml of acetone, under argon, was stirred and refluxed for 2 hours, then cooled and filtered. The filtrate was evaporated, the residue triturated with ether, filtered, washed with ether and dried. The solid was heated to solution in 10 ml of ethyl acetate, filtered, cooled, and after one hour 20 ml of hexane was added and the reaction recooled. The solid was collected, washed with hexane and dried, giving 1.3 g of the desired intermediate, mp 158°–160° C.

EXAMPLE 5

4-(Chloroacetyl)-4,5,6,7-tetrahydro-7-[3-(trifluoromethyl)phenyl]pyrazolo]1,5-a]pyrimidine-3-carbonitrile A 9.0 g portion of 4,5-dihydro-7-[3-(trifluoromethyl)-phenyl]pyrazolo[1,5-a]pyrimidine-3-carbonitrile in 90 ml of trifluoroacetic acid was stirred under argon and heated to 60°–65° C. A 10.8 ml portion of triethylsilane was added and the mixture was stirred at 60°–65° C. for 5.5 hours, then allowed to stand at room temperature overnight. The mixture was poured into 300 ml of 25% aqueous potassium hydroxide containing cracked ice and extracted three times with chloroform. The extracts were combined, washed with saturated sodium chloride, dried, concentrated to 200 ml and filtered through nydrous magnesium silicate. The solvent was evaporated and the residue triturated with ether and dried, giving 5.9 g of 4,5,6,7-tetrahydro-7-[3]trifluoromethyl)-phenyl]pyrazolo[1,5a]pyrimidine-3-carbonitrile.

A mixture of 5.9 g of the above compound and 10.2 g of chloroacetic anhydride in 60 ml of toluene, under argon, was stirred at reflux for 18 hours, then the solvent was removed in vacuo on a steam bath. The residual oil was dissolved in 25 ml of chloroform, filtered through hydrous magnesium silicate and concentrated to an oil. This oil was added to ether and the solid collected, giving the desired intermediate, mp 157°–159° C.

EXAMPLE 6

4-(Chloroacetyl)-7-(3-fluorophenyl)-4,5-dihydropyrazolo[1.5-a-a]pyrimidine-3-carbonitrile 7(3-Fluorophenyl)pyrazolo[1,5-a]pyrimidine-3-carbonitrile was reacted as described in Example 3, giving 6 g of the desired intermediate, mp 190°–193° C.

EXAMPLE 7

4-(Chloroacetyl)-4,5-dihydro-7-(3-nitrophenyl)-pyrazolo[1,5a]pyrimidine-3-carbonitrile 7-(3-Nitrophenyl)pyrazolo[1,5a]pyrimidine-3-carbonitrile was reacted as described in Example 3, giving 0.9 g of the desired intermediate, mp 164°–167° C.

EXAMPLE 8

4-(Chloroacetyl)-7-(4-chlorophenyl)-4,5-dihydropyrazolo]1,5-a][pyrimidine-3-carbonitrile 7-(4-Chlorophenyl)pyrazolo[1,5-a]pyrimidine-3-carbonitrile was reacted as described in Example 3, giving 12.44 g of the desired intermediate, mp 198°–199° C.

EXAMPLE 9

4-(Chloroacetyl)-7-(2,5-dichlorophenyl)-4.5-dihydropyrazolo[1.5-]pyrimidine-3-carbonitrile 7-(2,5-Dichlorophenyl)pyrazolo[1,5-a]pyrimidine-3-carbonitrile was reacted as described in Example 3, giving 39.3 g of the desired intermediate, mp 235°–236° C.

EXAMPLE 10

4-(Chloroacetyl)-4,5-dihydro-6-methyl-7-[3-(trifluoromethyl)phenyl]pyrazolo[1,5-a]-pyrimidine-3-carbonitrile 6-Methyl-7-[3-(trifluoromethyl)phenyl]pyrazolo[1,5-a]pyrimidine-3-carbonitrile was reacted as described in Example 3, giving 39.3 g of the desired intermediate, mp 178°–182° C.

EXAMPLE 11

4-(Chloroacetyl)-4,5-dihydro-5-methyl-7-[3-(trifluoromethyl)phenyl]pyrazolo[1,5-a]-pyrimidine-3-carbonitrile 5-Methyl-7-[3-(trifluoromethyl)phenyl]pyrazolo[1,5-a]pyrimidine-3-carbonitrile was reacted as described in Example 3, giving 6.2 g of the desired intermediate, mp 160°–163° C.

EXAMPLE 12

4-(Chloroacetyl)-7-(3-chlorophenyl)-4,5-dihydro-6-methylpyrazolo[1,5a]pyrimidine-3-carbonitrile 7(3-Chlorophenyl)-4,5-dihydro-6-methylpyrazolo[1,5a]pyrimidine-3-carbonitrile was reacted as described in Example 3, giving 12.5 g of the desired intermediate, mp 132°–135° C.

EXAMPLE 13

4-(Chloroacetyl)-4,5-dihydro-7-[3(trifluoromethyl)-phenyl]pyrazolo[1,5-a]pyrimidine-3-carboxylic acid, ethyl ester A 100 g portion of ethyl (ethoxymethylene)cyanoacetate was carefully poured into a solution of 50 ml of 85% hydrazine hydrate in 115 ml of water. The mixture was stirred for one hour, then cooled in an ice bath. The crystals which formed were collected, dissolved in dichloromethane, filtered through hydrous magnesium silicate, the filtrate cooled in an ice bath and hexane added. The resulting crystals were collected (40.9 g).

The above crystals and 62.7 g of 3-dimethylamino-3'-(trifluoromethyl)acrylophenone in 250 ml of acetic acid were stirred and heated at reflux for 16 hours and then evaporated to an oil. The oil was dissolved in 500 ml of dichloromethane and washed with aqueous sodium bicarbonate. Then the organic layer was dried, filtered and evaporated to an oil. This oil was dissolved in isopropanol on a steam bath then placed in an ice bath overnight. Filtration gave 67.1 g of white crystals.

The above 67.1 g of crystals were dissolved in 250 ml of glacial acetic acid and 35.5 g of sodium cyanoborohydride were added under nitrogen. The mixture was stirred for 3 hours and then evaporated to an oil. The oil was dissolved in dichloromethane, washed with aqueous sodium bicarbonate and on standing a solid formed. The solid was dissolved in 500 ml of isopropanol with heating, then chilled giving 50.3 g of solid.

To 6.8 g of the above solid and 4.0 g of 1,8-bis(dimethylamino)naphthalene,N,N,N',N',-tetramethyl-1,8-naphthalenediamine in 100 ml of dry tetrahydrofuran, was added with stirring, 4.50 g of chloroacetyl chloride in 100 ml of dry tetrahydrofuran, dropwise over 2 hours under a nitrogen atmosphere. The mixture was stirred overnight and the filtered. The filtrate was evaporated to a semi-solid and this was crystallized from ether to give 5.0 g of the desired intermediate, mp 141°–142° c.

EXAMPLE 14

4-(Chloroacetyl)-7-(4-chlorophenyl)-4.5-dihydro-6-methylpyrazolo[1,5a]pyrimidine-3-carbonitrile A 10 g solution of 7-(4-chlorophenyl)-4,5-dihydro-6-methylpyrazolo[1,5-a]pyrimidine-3-carbonitrile and 9 g of [1,8-bis(dimethylamino)naphthalene, N,N,N',N'-tetramethyl-1,8-naphthalenediamine] in 300 ml of dry tetrahydrofuran under nitrogen was mixed and 6 ml of chloroacetyl chloride in 70 ml of dry tetrahydrofuran was added over 15 minutes with stirring. The mixture was stirred at reflux for 5.5 hours, then at room temperature overnight and then filtered. The filtrate was concentrated to an oil. This oil was triturated with ether, the solid collected and dried, giving 10 g of the desired intermediate, mp 138°–140° C.

EXAMPLE 15

7-(4-Chlorophenyl)-4-(iodoacetyl)-4,5-dihydropyrazolo[1,5-a]pyrimidine-3-carbonitrile A mixture of 15.67 g of (4-chloroacetyl)-7-(4-chlorophenyl)-4,5-dihydropyrazolo[1,5-a]-pyrimidine-3-carbonitrile and 15.61 g of potassium iodine in 150 ml of acetone was heated and stirred at reflux for 6.5 hours and then filtered. The filtrate was evaporated and the residue triturated with ether, giving 4.51 g of the desired intermediate.

EXAMPLE 16

4,5-Dihydro-4-[(4-methyl-1-piperazinyl)acetyl]-7-[3-(trifluoromethyl)phenyl]pyrazolo[1,5-]-pyrimidine-3-carbonitrile A mixture of 1.3 g of N-methylpiperazine, 4.4 g of 4-(chloroacetyl)-4,5-dihydro-7-[3-(trifluoromethyl)phenyl]pyrazolo[1,5a]pyrimidine-3-carbonitrile and 1.5 g of sodium carbonate in 75 ml of toluene was refluxed for 4 hours, then allowed to stand at room temperature overnight. The mixture was treated with 30 ml of 1N sodium hydroxide and then phases were separated. The aqueous phase was extracted twice with chloroform. The organic phases were combined, washed with water, dried, filtered and concentrated. The residue was heated to solution in 50 ml of ethyl acetate, filtered and cooled. The crystalline solid was collected, washed with ethyl acetate and hexane and dried, giving 1.8 g of the desired product, mp 178°–180 ° C.

Following the general procedure of Example 16, using the intermediate of Examples 1–15 and 26 and the indicated piperazines, the products of Example 17–76 found in Table VIII were obtained.

TABLE VIII

| Example | Piperazine | Product | MP °C. |
|---|---|---|---|
| 17 | N-benzyl | 4,5-Dihydro-4-[[4-(phenylmethyl)-1-piperazinyl]-acetyl]-7-[3-(trifluoromethyl)phenyl]pyrazolo[1,5-a]-pyrimidine-3-carbonitrile | 200–202 |
| 18 | 3-chlorobenzyl | 4-[[4-[(3-Chlorophenyl)methyl]-1-piperazinyl]acetyl]-4,5-dihydro-7-[3-(trifluoromethyl)phenyl]pyrazolo-[1,5-a]pyrimidine-3-carbonitrile | 185–187 |
| 19 | 2,6-dichlorobenzyl | 4-[[4-[(2,6-Dichlorophenyl)methyl]-1-piperazinyl]-acetyl]-4,5-dihydro-7-[3-(trifluoromethyl)phenyl]-pyrazolo[1,5-a]pyrimidine-3-carbonitrile | 179–181 |
| 20 | 3-methoxybenzyl | 4,5-Dihydro-4-[[4-[(3-methoxyphenyl)methyl]-1-piperazinyl]acetyl]-7-[3-(trifluoromethyl)phenyl]pyrazolo-[1,5-a]pyrimidine-3-carbonitrile | 160–162 |
| 21 | 4-chlorophenyl-benzyl | 4-[[4-[(4-Chlorophenyl)phenylmethyl]-1-piperazinyl]-acetyl]-4,5-dihydro-7-[3-(trifluoromethyl)phenyl]-pyrazolo[1,5-a]pyrimidine-3-carbonitrile | 177–179 |
| 22 | 3,4-dichlorophenyl | 4-[[4-(3,4-Dichlorophenyl)-1-piperazinyl]acetyl]-4,5-dihydro-7-[3-(trifluoromethyl)phenyl]pyrazolo[1,5-a]-pyrimidine-3-carbonitrile | 180–182 |
| 23 | 1,3-benzodioxol-5-ylmethyl | 4-[[4-(1,3-Benzodioxol-5-ylmethyl)-1-piperazinyl]-acetyl]-4,5-dihydro-7-[3-(trifluoromethyl)phenyl]-pyrazolo[1,5-a]pyrimidine-3-carbonitrile | 173–175 |
| 24 | N-cyclohexyl | 4-[(4-Cyclohexyl-1-piperazinyl)acetyl]-4,5-dihydro-7-[3-(trifluoromethyl)phenyl]pyrazolo[1,5-a]pyrimidine-3-carbonitrile | 210–212 |
| 25 | N-phenyl | 4,5-Dihydro-4-[(4-phenyl-1-piperazinyl)acetyl]-7-[3-(trifluoromethyl)phenyl]pyrazolo[1,5-a]pyrimidine-3-carbonitrile | 179–180 |
| 26 | 3-chlorophenyl | 4-[[4-(3-Chlorophenyl)-1-piperazinyl]acetyl]-4,5-dihydro-7-[3-(trifluoromethyl)phenyl]pyrazolo[1,5-a]-pyrimidine-3-carbonitrile | 157–158 |
| 27 | N-benzyl | 4,5-Dihydro-4-[1-oxo-3-[4-(phenylmethyl)-1-piperazinyl]propyl]-7-[3-(trifluoromethyl)phenyl]pyrazolo-[1,5-a]pyrimidine-3-carbonitrile | 106–108 |
| 28 | 1-(2-pyrimidinyl) | 4,5-Dihydro-4-[[4-(2-pyrimidinyl)-1-piperazinyl]-acetyl]-7-[3-(trifluoromethyl)phenyl]pyrazolo[1,5-a]-pyrimidine-3-carbonitrile | 169–171 |
| 29 | 1-(2-pyridinyl) | 4,5-Dihydro-4-[[4-(2-pyridinyl)-1-piperazinyl]acetyl-7-[3-(trifluoromethyl)phenyl]pyrazolo[1,5-a]pyrimidine-3-carbonitrile | 168–170 |
| 30 | 3-(trifluoromethyl)phenyl | 4,5-Dihydro-7-[3-(trifluoromethyl)phenyl]-4-[[4-[3-(trifluoromethyl)phenyl]-1-piperazinyl]acetyl]pyrazolo[1,5-a]pyrimidine-3-carbonitrile | 145–146 |
| 31 | 4-fluorophenyl | 4-[[4-(4-Fluorophenyl)-1-piperazinyl]acetyl]-4,5-dihydro-7-[3-(trifluoromethyl)phenyl]pyrazolo[1,5-a]-pyrimidine-3-carbonitrile | 183–184 |
| 32 | 2-methoxyphenyl | 4,5-Dihydro-4-[[4-(2-methoxyphenyl)-1-piperazinyl]-acetyl]-7-[3-(trifluoromethyl)phenyl]pyrazolo[1,5-a]-pyrimidine-3-carbonitrile | 164–165 |
| 33 | 3-dimethylamino-propyl | 4-[[4-[3-(Dimethylamino)propyl]-1-piperazinyl]acetyl]-4,5-dihydro-7-[3-(trifluoromethyl)phenyl]pyrazolo-[1,5-a]pyrimidine-3-carbonitrile | 146–148 |
| 34 | 2-propynyl | 4,5-Dihydro-4-[[4-(2-propynyl)-1-piperazinyl]acetyl]-7-[3-(trifluoromethyl)phenyl]pyrazolo[1,5-a]pyrimidine-3-carbonitrile | 143–145 |
| 35 | 4-chlorobenzyl | 4-[3-[4-[(Chlorophenyl)methyl]-1-piperazinyl]-1-oxopropyl]-4,5-dihydro-7-[3-(trifluoromethyl)phenyl]-pyrazolo[1,5-a]pyrimidine-3-carbonitrile | 99–101 |
| 36 | 4-morpholinyl-2-oxoethyl | 4,5-Dihydro-4-[[4-[2-(4-morpholinyl)-2-oxoethyl]-1-piperazinyl]acetyl]-7-[3-(trifluoromethyl)phenyl]-pyrazolo[1,5-a]pyrimidine-3-carbonitrile | 179–181 |
| 37 | N-(1-methylethyl)-2-oxoethyl | 4-[2-[3-Cyano-7-[3-(trifluoromethyl)phenyl]pyrazolo-[1,5-a]pyrimidine-4(5H)-yl]-2-oxoethyl-N-(1-methylethyl)-1-piperazineacetamide | 117–119 |
| 38 | (1-pyrrolidinyl)-2-oxoethyl | 4,5-Dihydro-4-[[4-[2-oxo-2-(1-pyrrolidinyl)ethyl]-1-piperazinyl]acetyl]-7-[3-(trifluoromethyl)phenyl]- | 159–162 |

TABLE VIII-continued

| Example | Piperazine | Product | MP °C. |
|---|---|---|---|
| | | pyrazolo[1,5-a]pyrimidine-3-carbonitrile | |
| 39 | 4-chlorobenzyl | 4-[4-[(4-Chlorophenyl)methyl]-1-piperazinyl]acetyl]-7-[3-(trifluoromethyl)phenyl]pyrazolo[1,5-a]pyrimidine-3-carbonitrile | 205-207 |
| 40 | bis(4-fluoro-phenyl)methyl | 4-[[4-[Bis(4-fluorophenyl)methyl]-1-piperazinyl]-acetyl]-4,5-dihydro-7-[3-(trifluoromethyl)phenyl]-pyrazolo[1,5-a]pyrimidine-3-carbonitrile | 177-179 |
| 41 | 2-cyclohexylethyl | 4-[[4-(2-Cyclohexylethyl)-1-piperazinyl]acetyl]-4,5-dihydro-7-[3-(trifluoromethyl)phenyl]pyrazolo-[1,5-a]pyrimidine-3-carbonitrile | 208-210 |
| 42 | carboxylic acid, ethyl ester | 4-[2-[3-Cyano-7-[3-(trifluoromethyl)phenyl]pyrazolo-[1,5-a]pyrimidine-4(5H)-yl]-2-oxoethyl]-1-piperazine-carboxylic acid, ethyl ester | 75-78 |
| 43 | 3-chlorobenzyl | 7-(3-Chlorophenyl)-4-[[4-[(3-chlorophenyl)methyl]-1-piperazinyl]acetyl]-4,5-dihydropyrazolo[1,5-a]pyrimidine-3-carbonitrile | 160-162 |
| 44 | benzyl | 7-(3-Chlorophenyl)-4,5-dihydro-4-[[4-(phenylmethyl)-1-piperazinyl]acetyl]pyrazolo[1,5-a]pyrimidine-3-carbonitrile | 165-166 |
| 45 | 4-chlorophenyl-benzyl | 7-(3-Chlorophenyl)-4-[[4-[(4-chlorophenyl)phenyl-methyl]-1-piperazinyl]acetyl]-4,5-dihydropyrazolo-[1,5-a]pyrimidine-3-carbonitrile | 159-161 |
| 46 | N-benzyl | 4,5,6,7-Tetrahydro-4-[[4-(phenylmethyl)-1-pipera-zinyl]acetyl]-7-[3-(trifluoromethyl)phenyl]pyrazolo-[1,5-a]pyrimidine-3-carbonitrile | 164-166 |
| 47 | 2-propenyl | 4,5-Dihydro-4-[[4-(2-propenyl)-1-piperazinyl]acetyl]-7-[3-(trifluoromethyl)phenyl]pyrazolo[1,5-a]pyrimidine-3-carbonitrile | 167-169 |
| 48 | N-benzyl | 7-(3-Fluorophenyl)-4,5-dihydro-4-[[4-(phenylmethyl)-1-piperazinyl]acetyl]pyrazolo[1,5-a]pyrimidine-3-carbonitrile | 138-140 |
| 49 | 4-chlorobenzyl | 4-[[4-[(4-Chlorophenyl)methyl]-1-piperazinyl]acetyl]-7-(3-fluorophenyl)-4,5-dihydropyrazolo[1,5-a]pyrimidine-3-carbonitrile | 160-165 |
| 50 | N-benzyl | 4,5-Dihydro-7-(3-nitrophenyl)-4-[[4-(phenylmethyl)-1-piperazinyl]acetyl]pyrazolo[1,5-a]pyrimidine-3-carbonitrile | 155-157 |
| 51 | 1-methylethyl | 4,5-Dihydro-4-[[4-(1-methylethyl)-1-piperazinyl]-acetyl]-7-[3-(trifluoromethyl)phenyl]pyrazolo[1,5-a]-pyrimidine-3-carbonitrile | 187-189 |
| 52 | N-cyclobutyl | 4-[(4-Cyclobutyl-1-piperazinyl)acetyl]-4,5-dihydro-7-[3-(trifluoromethyl)phenyl]pyrazolo[1,5-a]pyrimidine-3-carbonitrile | 188-190 |
| 53 | 3-chlorobenzyl | 4-[[4-[(3-Chlorophenyl)methyl]-1-piperazinyl]acetyl]-4,5,6,7-tetrahydro-7-[3-(trifluoromethyl)phenyl]-pyrazolo[1,5-a]pyrimidine-3-carbonitrile | 160-162 |
| 54 | 2,6-dichloro-benzyl | 4-[[4-[(2,6-Dichlorophenyl)methyl]-1-piperazinyl]-acetyl]-4,5,6,7-tetrahydro-7-[3-(trifluoromethyl)-phenyl]pyrazolo[1,5-a]pyrimidine-3-carbonitrile | 140-142 |
| 55 | 3-phenoxypropyl | 4,5-Dihydro-4-[[4-(3-phenoxypropyl)-1-piperazinyl]-acetyl]-7-[3-(trifluoromethyl)phenyl]pyrazolo[1,5-a]-pyrimidine-3-carbonitrile | 139-141 |
| 56 | 4-chlorobenzyl | 4-[[4-[(4-Chlorophenyl)methyl]-1-piperazinyl]acetyl]-4,5,6,7-tetrahydro-7-[3-(trifluoromethyl)phenyl]-pyrazolo[1,5-a]pyrimidine-3-carbonitrile | 165-167 |
| 57 | 3-phenoxypropyl | 4,5,6,7-Tetrahydro-4-[[4-(3-phenoxypropyl)-1-pipera-zinyl]acetyl-7-[3-(trifluoromethyl)phenyl]pyrazolo-[1,5-a]pyrimidine-3-carbonitrile | 113-115 |
| 58 | N-benzyl | 7-(4-Chlorophenyl)-4,5-dihydro-4-[[4-(phenylmethyl)-1-piperazinyl]acetyl]pyrazolo[1,5-a]pyrimidine-3-carbonitrile | 182-183 |
| 59 | 2-(trifluoro-methyl)benzyl | 7-(4-Chlorophenyl)-4,5-dihydro-4-[[4-[[2-(trifluoro-methyl)phenyl]methyl]-1-piperazinyl]acetyl]pyrazolo-[1,5-a]pyrimidine-3-carbonitrile | 144-145 |
| 60 | 2-methoxyphenyl | 7-(4-Chlorophenyl)-4,5-dihydro-4-[[4-(2-methoxy-phenyl)-1-piperazinyl]acetyl]pyrazolo[1,5-a]pyrimidine-3-carbonitrile | 179-180 |
| 61 | bis(4-fluoro-phenyl)methyl | 4-[[4-[Bis(4-fluorophenyl)methyl]-1-piperazinyl]-acetyl]-7-(4-chlorophenyl)-4,5-dihydropyrazolo[1,5-a]-pyrimidine-3-carbonitrile | 108-110 |
| 62 | N-benzyl | 7-(2,5-Dichlorophenyl)-4,5-dihydro-4-[[4-(phenyl-methyl)-1-piperazinyl]acetyl]pyrazolo[1,5-a]pyrimidine-3-carbonitrile | 173-174 |
| 63 | 3-phenoxypropyl | 7-(4-Chlorophenyl)-4,5-dihydro-4-[[4-(3-phenoxy-propyl)-1-piperazinyl]acetyl]pyrazolo[1,5-a]pyrimidine-3-carbonitrile | 175-177 |
| 64 | 4-chlorobenzyl | 7-(4-Chlorophenyl)-4-[[4-[(4-chlorophenyl)methyl]-1-piperazinyl]acetyl]-4,5-dihydropyrazolo[1,5-a]-pyrimidine-3-carbonitrile | 178-179 |
| 65 | 1,3-benzodioxol-5-yl | 4-[[4-(1,3-Benzodioxol-5-yl)-1-piperazinyl]acetyl]-7-(2,5-dichlorophenyl)-4,5-dihydropyrazolo[1,5-a]- | 173-174 |

TABLE VIII-continued

| Example | Piperazine | Product | MP °C. |
|---|---|---|---|
| 66 | 2,5-dimethylphenyl | pyrimidine-3-carbonitrile<br>7-(2,5-Dichlorophenyl)-4-[[4-(2,5-dimethylphenyl)-1-piperazinyl]acetyl]-4,5-dihydropyrazolo[1,5-a]pyrimidine-3-carbonitrile | 166–167 |
| 67 | N-methyl | 7-(2,5-Dichlorophenyl))-4,5-dihydro-4-[(4-methyl-1-piperazinyl)acetyl]pyrazolo[1,5-a]pyrimidine-3-carbonitrile | 182–185 |
| 68 | N-benzoyl | 4-[(4-Benzoyl-1-piperazinyl)acetyl]-4,5-dihydro-7-[3-(trifluoromethyl)phenyl]pyrazolo[1,5-a]pyrimidine-3-carbonitrile | 183–185 |
| 69 | 2-methoxyphenyl | 7-(2,5-Dichlorophenyl)-4,5-dihydro-4-[[4-(2-methoxyphenyl)-1-piperazinyl]acetyl]pyrazolo[1,5-a]pyrimidine-3-carbonitrile | 121–122 |
| 70 | 2-furanylcarbonyl | 7-(2,5-Dichlorophenyl)-4,5-dihydro-4-[[4-(2-furanylcarbonyl)-1-piperazinyl]acetyl]pyrazolo[1,5-a]pyrimidine-3-carbonitrile | 142–144 |
| 71 | N-benzyl | 7-(2,5-Dichlorophenyl)-4,5-dihydro-4-[1-oxo-3-[4-(phenylmethyl)-1-piperazinyl]propyl]pyrazolo[1,5-a]-pyrimidine-3-carbonitrile | 94–95 |
| 72 | N-benzyl | 4,5-Dihydro-5-methyl-4-[[4-(phenylmethyl)-1-piperazinyl]acetyl-7-[3-(trifluoromethyl)phenyl]pyrazolo-[1,5-a]pyrimidine-3-carbonitrile | 129–131 |
| 73 | N-hydroxyethyl | 4,5-Dihydro-4-[[4-(2-hydroxyethyl)-1-piperazinyl]-acetyl]-6-methyl-7-[3-(trifluoromethyl)phenyl]pyrazolo[1,5-a]pyrimidine-3-carbonitrile | 178–179 |
| 74 | N-methyl | 4,5-Dihydro-4-[(4-methyl-1-piperazinyl)acetyl]-7-[3-(trifluoromethyl)phenyl]pyrazolo[1,5-a]pyrimidine-3-carboxamide | 164–166 |
| 75 | N-benzyl | 4,5-Dihydro-4-[[4-(phenylmethyl)-1-piperazinyl]-acetyl]-7-[3-(trifluoromethyl)phenyl]pyrazolo[1,5-a]-pyrimidine-3-carboxamide | 152–154 |
| 76 | N-benzyl | 3-Bromo-4,5-dihydro-4-[[4-(phenylmethyl)-1-piperazinyl]acetyl]-7-[3-(trifluoromethyl)phenyl]pyrazolo-[1,5-a]pyrimidine | 127–129 |

EXAMPLE 77

4,5-Dihydro-4-[(4-methyl-1-piperazinyl)acetyl]-7-[3-(trifluoromethyl)phenyl]pyrazole[1,5-a]-pyrimidine-3-carbonitrile, dihydrochloride 4,5-Dihydro-4-[(4-methyl-1-piperazinyl)acetyl]-7-[3-(trifluoromethyl-phenyl]pyrazolo[1,5, a]pyrimidine-3-carbonitrile was dissolved in hot ethyl acetate and treated with dilute ethanolic hydrochloric acid. Cooling produced a solid which was collected, washed with ether and dried. This solid was heated to boiling in 60 ml of acetonitrile, filtered and the filtrate diluted with 60 ml of ether and refrigerated. The solid was collected, washed with ether and dried, giving 600 mg of the desired product, mp 198° C. (eff.)

Following the general procedure of Example 77 using various organic and inorganic solvents, the products of Examples 78 through 95 found in Table IX were obtained.

TABLE IX

| Example | Base Example | Product | MP°C. |
|---|---|---|---|
| 78 | 17 | 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile, dihydrochloride | 224–226 |
| 79 | 20 | 4,5-Dihydro-4-[[4-[(3-methoxyphenyl)methyl]-1-piperazinyl]-acetyl]-7-[3-(trifluoromethyl)phenyl]pyrazolo[1,5-a]pyrimidine-3-carbonitrile, dihydrochloride | 226–228 |
| 80 | 19 | 4-[[4-[(2,6-Dichlorophenyl)methyl]-1-piperazinyl]acetyl]-4,5-dihydro-7-[3-(trifluoromethyl)phenyl]pyrazolo[1,5-a]pyrimidine-3-carbonitrile, dihydrochloride | 220–222 |
| 81 | 18 | 4-[[4-[(3-Chlorophenyl)methyl]-1-piperazinyl]acetyl]-4,5-dihydro-7-[3-(trifluoromethyl)phenyl]pyrazolo[1,5-a]pyrimidine-3-carbonitrile, dihydrochloride | 220–222 |
| 82 | 22 | 4-[[4-(3,4-Dichlorophenyl)-1-piperazinyl]acetyl]-4,5-dihydro-7-[3-(trifluoromethyl)phenyl]pyrazolo[1,5-a]pyrimidine-3-carbonitrile, hydrochloride | 260–262 |
| 83 | 24 | 4-[(4-Cyclohexyl-1-piperazinyl)acetyl]-4,5-dihydro-7-[3-(trifluoromethyl)phenyl]pyrazolo[1,5-a]pyrimidine-3-carbonitrile, dihydrochloride | 241–243 |
| 84 | 28 | 4,5-Dihydro-4-[[4-(2-pyrimidinyl)-1-piperazinyl]acetyl]-7-[3-(trifluoromethyl)phenyl]pyrazolo[1,5-a]pyrimidine-3-carbonitrile, hydrochloride | 235–237 |
| 85 | 35 | 4-[3-[(4-Chlorophenyl)methyl]-1-piperazinyl]-1-oxopropyl]-4,5-dihydro-7-[3-(trifluoromethyl)phenyl]pyrazolo[1,5-a]pyrimidine-3-carbonitrile, dihydrochloride | 254–256 |
| 86 | 41 | 4-[[4-(2-Cyclohexylethyl)-1-piperazinyl]acetyl]-4,5-dihydro-7-[3-(trifluoromethyl)phenyl]pyrazolo[1,5-a]pyrimidine-3-carbonitrile, dihydrochloride | 235–237 |
| 87 | 39 | 4-[[4-[(4-Chlorophenyl)methyl]-1-piperazinyl]acetyl]-4,5- | 219–221 |

TABLE IX-continued

| Example | Base Example | Product | MP°C. |
|---|---|---|---|
| | | dihydro-7-[3-(trifluoromethyl)phenyl]pyrazolo[1,5-a]pyrimidine-3-carbonitrile, dihydrochloride | |
| 88 | 40 | 4-[[4-[Bis(4-Fluorophenyl)methyl]-1-piperazinyl]acetyl]-4,5-dihydro-7-[3-(trifluoromethyl)phenyl]pyrazolo[1,5-a]pyrimidine-3-carbonitrile, dihydrochloride | 255-258 |
| 89 | 46 | 4,5,6,7-Tetrahydro-4-[[4-(phenylmethyl)-1-piperazinyl]acetyl]-7-[3-(trifluoromethyl)phenyl]pyrazolo[1,5-a]pyrimidine-3-carbonitrile, dihydrochloride | 195-197 |
| 90 | 51 | 4,5-Dihydro-4-[[4-(1-methylethyl)-1-piperazinyl]acetyl]-7-[3-(trifluoromethyl)phenyl]pyrazolo[1,5-a]pyrimidine-3-carbonitrile, dihydrochloride | 205-208 |
| 91 | 52 | 4-[(4-Cyclobutyl-1-piperazinyl)acetyl]-4,5-dihydro-7-[3-(trifluoromethyl)phenyl]pyrazolo[1,5-a]pyrimidine-3-carbonitrile, dihydrochloride | 227-229 |
| 92 | 67 | 7-(1,5-Dichlorophenyl)-4,5-dihydro-4-[(4-methyl-1-piperazinyl)acetyl]pyrazolo[1,5-a]pyrimidine-3-carbonitrile, dihydrochloride | 248-250 |
| 93 | 68 | 4-[(4-Benzoyl-1-piperazinyl)acetyl]-4,5-dihydro-7-[3-(trifluoromethyl)phenyl]pyrazolo[1,5-a]pyrimidine-3-carbonitrile, hydrochloride | 243-245 |
| 94 | 69 | 4,5-Dihydro-4-[[4-(phenylmethyl)-1-piperazinyl]acetyl]-7-[3-(trifluoromethyl)phenyl]pyrazolo[1,5-a]pyrimidine-3-carbonitrile, hydrochloride | 160-162 |
| 95 | 72 | 4,5-Dihydro-5-methyl-4-[[4-(phenylmethyl)-1-piperazinyl]acetyl]-7-[3-(trifluoromethyl)phenyl]pyrazolo[1,5-a]pyrimidine-3-carbonitrile, dihydrochloride | 190-192 |

EXAMPLE 96

4-[[4-(2-Furanylcarbonyl)-1-piperazinyl]acetyl]-4,5-dihydro-7-[(3-trifluoromethyl)phenyl]pyrazolo[1,5-a]pyrimidine-3-carbonitrile, hydrochloride A 2.2 g portion of 2-furanylcarbonyl piperazine, 4 g of 4-(chloroacetyl)-4,5-dihydro7[3-(trifluoromethyl)phenyl]pyrazolo[1,5-a]-pyrimidine-3-carbonitrile and 1.6 g of sodium carbonate in 60 ml of toluene was reacted as described in Example 16, giving 3.3 g of the base as a hygroscopic solid. This solid was dissolved in ethanol, 10 ml of 3N ethanolic hydrogen chloride was added and the mixture was stirred. The solid was collected, washed with ethanol, ether, and then dried to give 1.2 g of the desired product, mp 240°-243° C.

EXAMPLE 97

4-[[4-[2-(Dimethylamino)ethyl]-1-piperazinyl]acetyl]4,5-dihydro-7-[3-(trifluoromethyl)phenyl]-pyrazolo[1,5-a]pyrimidine-3-carbonitrile, dihydrochloride A mixture of 1.7 g of 2-dimethylaminoethyl piperazine, 3.8 g of 4-(chloroacetyl)-4,5-dihydro-7-[3-trifluoromethyl)phenyl]pyrazolo[1,5-a]pyrimidine-3-carbonitrile, 1.2 g of sodium carbonate and 65 ml of toluene was reacted as described in Example 16, giving 3.2 g of solid. The solid was reacted with ethanolic hydrogen chloride, giving 170 mg of the desired product, m; 229°-231° C.

EXAMPLE 98

4,5-Dihydro-4-(1-piperazinylacetyl)-7-[3-(trifluoromethyl)phenyl]pyrazolo[1,5-a]pyrimidine-3-carbonitrile A mixture of 1.56 g of 4,5-dihydro-4-(iodoacetyl)-7-[3-(trifluoromethyl)phenyl]pyrazolo[1,5-a]pyrimidine-3-carbonitrile and 1 g of piperazine in 50 ml of dioxane, under argon, was heated was stirred at reflux for 18 hours. The reaction was cooled, the solid collected, removed by filtration and the filtrate evaporated. The residue was crystallized by trituration with ether giving 1.3 g of crystals. These crystals were heated to solution in 10 ml of ethyl acetate, diluted with 10 ml of hexane and filtered. The filtrate was cooled giving a solid which was collected, washed with hexane and dried, giving 400 mg of the desired product, mp 151°-154° C.

EXAMPLE 99

4-[2-[3-Cyano-7-[3-(trifluoromethyl)phenyl]pyrazolo-[1,5-a]pyrimidine-4(5H)-yl]-2-oxoethyl]-N-phenyl-1-piperazinecarboxamide A mixture of 3.5 g of 4,5-dihydro-4-(1piperazinylacetyl)-7-[3-(trifluoromethyl)phenyl]-pyrazolo[1,5-a]pyrimidine-3-carbonitrile an d1 g of phenyl isocyanate in 50 ml of acetone was stirred and refluxed for 18 hours, then cooled and filtered. The filtrate was evaporated on a steam bath and the residue repeatedly triturated with ether. The solid was dissolved with warming in 15 ml of chloroform, then filtered and 15 ml of hexane was added. The crystals were collected, washed with hexane and dried, giving 2.1 g of the desired product, mp 184°-187° C.

EXAMPLE 100

N-(5-Chloro-2-methoxyphenyl)-4-[2-[3-cyano-7-[3-(trifluoromethyl)phenyl]pyrazolo[1,5-a]-pyrimidin-4(5H)-yl]-2-oxoethyl]-1-piperazineacetamide A mixture of 3.5 g of 4,5-dihydro-4-(1-piperazinylacetyl)-7-[3-(trifluoromethyl)phenyl]-pyrazolo]1,5-a]pyrimidine-3-carbonitrile, 2 g of 2-chloro-N-(5chloro-2-methoxy phenyl)acetamide and 900 mg of sodium carbonate in 50 ml of toluene was refluxed with stirring for 18 hours, then cooled and made basic with 15 ml of 1N sodium hydroxide. The aqueous phase was separated and extracted twice with chloroform. The organic phases were combined, washed with water, dried, filtered and concentrated to dryness. The residue was triturated with ether, the solid collected, washed with ether and dried. This solid was heated to solution in 40 ml of acetonitrile, filtered and cooled. The solid was collected, washed with acetonitrile and ether and dried, giving 2.3 g of the desired product, m; 166°-168° C.

EXAMPLE 101

4-[2-[3-Cyano-7-[3-(trifluoromethyl)phenyl]pyrazolo-[1,5-a]pyrimidin-4-(5H)-yl]-2-oxoethyl]-N-[3-(trifluoromethyl)phenyl]-1-piperazinecarboxamide A mixture of 2.6 g of 3-(trifluoromethyl)phenyl isocyanate, 5.7 g of 4,5-dihydro-4-(1-piperazinylacetyl)-7-[3-(trifluoromethyl)phenyl]pyrazolo[1,5-a]pyrimidine-3-carbonitrile and 80 ml of acetone was heated at reflux for 18 hours, then concentrated to dryness. The residue was triturated with 20 ml of ether and the solid collected. The solid was dissolved with heating in 10 ml of ethyl acetate, diluted with 10 ml of hexane and then cooled. The solid was collected, washed with hexane and dried, giving 780 mg of the desired product, mp 147°–149° C.

EXAMPLE 102

4,5-Dihydro-4-[[4-(1-oxotetradecyl)-1-piperazinyl]acetyl]-7-[3-(trifluoromethyl)phenyl]pyrazolo[1,5-a]pyrimidine-3-carbonitrile To a mixture of 3 g of 4,5-dihydro-4(1-piperazinylacetyl)-7-[3-(trifluoromethyl)phenyl]-pyrazolo[1,5-a]pyrimidine-3-carbonitrile and 0.8 g of [1,8-bis(dimethylamino)naphthalene, N,N,N',N'-tetramethyl-1,8-naphthalene diamine] in 30 ml of dry tetrahydrofuran, under nitrogen, was added a solution of 1.75 g of myristoyl chloride in 10 ml of dry tetrahydrofuran. The mixture was stirred at reflux overnight, then at room temperature for 2 days. The solid was collected, washed with ether, then water and dried, giving 3 g of the desired product, m; 260°–263° C.

EXAMPLE 103

4,5-Dihydro-4-[[4-(tricyclo[3,3,1,1]dec-1-ylcarbonyl)-1-piperazinyl]acetyl]-7-[3-(trifluoromethyl)phenyl]-pyrazolo[1.5-a]pyrimidine3-carbonitrile The procedure of Example 102 was followed using 1.5 of adamantanecarbonyl chloride, giving 2.3 g of the desired product, mp 194°–200° C.

EXAMPLE 104

4-[2-[3-Cyano-7-[3-(trifluoromethyl)phenyl]-pyrazolo[1,5-a]pyrimidin-4(5H)-yl]-2-oxoethyl]-N-(3,4-dichlorophenyl)-1-piperazinecarboxamide The procedure of Example 101 was followed, using 12.3 g of 3,4-dichlorophenyl isocyanate, giving 1.4 g of the desired product, mp 204°–206° C.

EXAMPLE 105

N-(3-Chlorophenyl)-4-[2-[3-cyano-7-[3-(trifluoromethyl)phenyl]pyrazolo[1,5-a]pyrimidin-4(5H)-yl]-2-oxoethyl]-1-piperazinecarboxamide The procedure of Example 101 was followed, using 1.8 g of 3-chlorophenyl isocyanate, giving 900 mg of the desired product, mp 182°–185° C.

EXAMPLE 106

N-[4-Chloro-3-(trifluoromethyl)phenyl]-4-[2-[3-cyano-7-[3-trifluoromethyl)phenylpyrazolo[1.5-a]pyrimidin-4(5H)-yl]-2-oxoethyl]-1-piperazinecarboxamide The procedure of Example 101 was followed, using 2.7 g of 4-chloro-3-(trifluoromethyl)phenyl isocyanate, giving 1.4 g of the desire compound, m; 214°–216° C.

EXAMPLE 107

4-[2-[3-Cyano-7-[3-(trifluororomethyl)phenyl]-pyrazolo[1,5-a]pyrimidin-4(5H)-yl]2-oxoethyl]-2,4-difluorophenyl)-1-piperazinecarboxamide The procedure of Example 101 was followed, using 1.4 g of 2,4difluorophenyl isocyanate, giving 2.6 g of the desired product, mp 142°–145° C.

EXAMPLE 108

4-[2-[3-Cyano-7-[3-(trifluoromethyl)phenyl]-pyrazolo[1,5-a]pyrimidin-4(5H)-yl]-2-oxoethyl]-N-(3-methylphenyl)-1-piperazinecarboxamide The procedure of Example 101 was followed, using 1.2 g of 3-methylphenyl isocyanate, giving 2.5 g of the desired product, mp 138°–140° C.

EXAMPLE 109

4,5-Dihydro-4-[[4-[4-(2-oxo-1-pyrrolidinyl)-2-butynyl]-1-piperazinyl]acetyl]-7-[3-(trifluoromethyl)phenyl]-pyrazolo[1.5-a]pyrimidine-3-carbonitrile A mixture of 3.1 g of 4,5-dihydro-4-(1piperazinylacetyl)-7-[3-(trifluoromethyl)phenyl]-pyrazolo[1,5-a]pyrimidine-3-carbonitrile, 255 mg of paraformaldehyde, 815 mg of 1-(2-propargyl)byrrolidine-2-one and 50 mg of cupric chloride in 30 ml of dioxane was refluxed under nitrogen, with stirring for 2 hours and then stirred overnight at room temperature. The mixture was concentrated and the residue acidified with 3 ml of 6N hydrochloric acid. A 10 ml portion of water was added and the mixture was shaken with ether until the oil was dissolved. The aqueous phase was separated, rewashed with ether, then made basic with 6 ml of 5N sodium hydroxide and extracted twice with, chloroform. The chloroform extracts were combined, washed with saturated salt solution, dried, filtered and concentrated to dryness. The residue was triturated with ether and the solid collected. This solid was dissolved with heating in 25 ml of ethyl acetate, filtered and cooled. The solid was collected, washed with hexane and dried, giving 2 g of the desired product mp 124°–126° C.

EXAMPLE 110

4,5-Dihydro-4-[[4-(phenylmethyl)-1-piperazinyl]acetyl]-7-[3-(trifluoromethyl)phenyl]pyrazolo[1.5-a]pyrimidine-3-carboxylic acid, ethyl ester. dihydrochloride A mixture of 2.065 g of 4-(chloroacetyl)4,5-dihydro-7-[3-(trifluoromethyl)phenyl]pyrazolo[1,5-a]pyrimidine-3-carboxylic acid, ethyl ester, 535 mg of [1,8-bis(-dimethylamino)naphthalene, N,N,N',N'-tetramethyl-1,8-naphthalenediamine],2.88 g of N-benzylpiperazine and 100 ml of dry ether was stirred at room temperature overnight and then filtered. The filtrate was evaporated, the residue dissolved in 300 ml of ether and 1 ml of concentrated hydrochloric acid in 50 ml of water was added. The solid was collected, giving 845 mg of the desired product, mp 228°–230° C.

EXAMPLE 111

4,5-Dihydro-6-methyl-4-[[4-(phenylmethyl)-1-piperazinyl]acetyl]-7-[3-(trifluoromethyl)phenyl]-pyrazolo[1.5-a]pyrimidine-3-carbonitrile. dihydrochloride A mixture of 3.4 g of 4-(chloroacetyl)4,5-dihydro-6-methyl-7-[3-(trifluoromethyl)phenyl]pyrazolo[1,5-a]pyrimidine-3-carbonitrile, 1.1 g of sodium carbonate, 1.7 g of N-benzylpiperazine and 115 ml of toluene was reacted as described in Example 16, giving the base form of the product which was converted to the dihydrochloride salt by the procedure of Example 97, giving 2.4 g, mg 204°-206° C.

EXAMPLE 112

4,5-Dihydro-6-methyl-4-[[4-(2-pyridinyl)-1-piperazinyl]acetyl]-7-[3-(trifluoromethyl)phenyl]pyrazolo[1,5-a]pyrimidine-3-carbonitrile A mixture of 2 g of 1-(2-pyridinyl)piperazine, 2 g of 4-(chloroacetyl)-4,5-dihydro-6-methyl-7-[3-(trifluoromethyl)phenyl]pyrazolo[1,5-a]pyrimidine-3-carbonitrile and 60 ml of acetone was refluxed on a steam bath for 8 hours and then evaporated. The residue was stirred in water and the solid collected. The solid was dissolved in dilute hydrochloric acid, filtered and the filtrate gasified with dilute ammonium hydroxide. The solid was collected, washed with water and dried in vacuo, giving 2.67 g of the desired product, mp 132°-134° C.

EXAMPLE 113

7-(3-Chlorophenyl)-4,5-dihydro-6-methyl-4-[[4-8-(phenylmethyl)piperazinyl]acetyl]pyrazolo[1,5-a]pyrimidine-3-carbonitrile, dihydrochloride A mixture of 3.1 g of 4-(chloroacetyl)-7-(3-chlorophenyl)-4,5-dihydro-6-methylpyrazolo[1,5-a]pyrimidine-3-carbonitrile, 1.1 g of sodium carbonate, 1.7 g of N-benzylpiperazine and 115 ml of toluene was reacted as described in Example 16, giving the base form of the product which was converted to the dihydrochloride salt by the procedure of Example 97, giving 1.3 g, mp 201°-203° C.

EXAMPLE 114

7-(4-Chlorophenyl)-4.5-dihydro-6-methyl-4[[4-(phenylmethyl)piperazinyl]acetyl]pyrazolo[1,5-a]pyrimidine-3-carbonitrile, dihydrochloride A mixture of 3.1 g of 4-(chloroacetyl)-7-(4-chlorophenyl)-4,5-dihydro-6-methylpyrazolo[1,5-a]pyrimidine-3-carbonitrile, 1.3 g of sodium carbonate, 2 g of N-benzylpiperazine and 130 ml of toluene was reacted as described in Example 16, giving the base form of the product which was converted to the dihydrochloride salt, by the procedure of Example 97, giving 1.5 g, mp 238°-240° C.

EXAMPLE 115

7-(4-Chlorophenyl)-4,5-dihydro-4-(1-piperazinylacetyl)pyrazolo[1.5-a]pyrimidine-3-carbonitrile, hydroiodide A mixture of 5 g of 7-(4-chlorophenyl)-4-(iodoacetyl)-4,5-dihydropyrazolo[1,5-a]pyrimidine-3-carbonitrile and 3.15 g of piperazine in acetone was heated at reflux for 6 hours, then at room temperature overnight and evaporated. The residue was taken up in water, evaporated and recrystallized from ethanol, giving 3.27 g of the desired product, mp 231°-232° C.

EXAMPLE 116

4,5-Dihydro-6-methyl-7-[3-(trifluoromethyl)phenyl]-4[[4[[3-(trifluoromethyl)phenyl]methyl]1-piperazinyl]acetyl]pyrazolo[1,5-a]pyrimidine3-carbonitrile, hydrochloride A mixture of 1.83 g of 4-(chloroacetyl)-7-[3(trifluoromethyl)phenyl]-4,5-dihydro-6methyl-pyrazolo[1,5-a]pyrimidine-3-carbonitrile, 1,5 g of 3(trifluoromethyl)benzylpiperazine, 2 g of potassium carbonate and 60 ml of toluene was reacted as described in Example 16, giving the base form of the product, which was converted to the hydrochloride salt by the procedure of Example 97, giving 1.78 g, mp 195°-198°.

EXAMPLE 117

4-[[4-[(2,6-Dichlorophenyl)methyl]-1-piperazinyl]acetyl]-4.5-dihydro-6-methyl-7-]3-(trifluoromethyl)-phenyl]pyrazolo[1,5-a]pyrimidine-3-carbonitrile, hydrochloride A mixture of 1 g, of 4-(chloroacetyl)-7-[3-(trifluoromethyl)phenyl]-4,5-dihydro-6-methyl-pyrazolo[1,5-a]pyrimidine-3-carbonitrile, 1 g of 2,6-dichlorobenzylpiperazine, 600 mg of potassium carbonate and 100 ml of toluene was reacted as described in Example 16, giving the base form of the product, which was converted to the hydrochloride salt by the procedure of Example 97, giving 1.66 g, mp 252°-254° C.

EXAMPLE 118

4-(Chloroacetyl)-4.5-dihydro-7-phenylpyrazolo[1,5-a]pyrimidine-3-carbonitrile

The above compound is prepared from 7-phenyl-pyrazolo[1,5-a]pyrimidine-3-carbonitrile by the procedure of Example 1.

EXAMPLE 119

4,5-Dihydro-4-[[4-(phenylmethyl)-1-piperazinyl)acetyl]-7-phenylpyrazolo[1,5-a]pyrimidine-3-carbonitrile The above compound is obtained from N-benzylpiperazine and 4-(chloroacetyl)-4,5-dihydro-7-phenyl-pyrazolo[1,5-a]pyrimidine-3-carbonitrile by the procedure of Example 16.

EXAMPLE 120

4-(Chloroacetyl)-4,5-dihydro-7-(3-methoxyphenyl)-pyrazolo[1,5-a]pyrimidine-3-carbonitrile The above compound is prepared from 7-(3-methoxyphenyl)pyrazolo[1,5-a]pyrimidine-3-carbonitrile by the procedure of Example 1.

EXAMPLE 121

4.5-Dihydro-4[[4-(phenylmethyl)-1-piperazinyl]acetyl]-7-(3-methoxyphenyl)pyrazolo[1,5-a]pyrimidine-3-carbonitrile The above compound is obtained form N-benzylpiperazine and 4 -(chloroacetyl)-4,5-dihydro-7-(3-methoxyphenyl)pyrazolo[1,5a]pyrimidine-3-carbonitrile by the procedure of Example 16.

EXAMPLE 122

3-Chloro-4-(chloroacetyl)-4,5-dihydro-7-[3-[trifluoromethyl)phenyl]pyrazolo[1,5-a]pyrimidine A 13.3 g portion of 3-chloro-7-[3-(trifluoromethyl)phenyl)pyrazolo[1,5-a]pyrimidine and 7 g of sodium cyanoborohydride in 50 ml of acetic acid, were reacted as described in Example 1, giving 6.7 g of 3-chloro-4,5-dihydro-7-[3-(trifluoromethyl) phenyl]pyrazolo[1,5-a]pyrimidine.

A 4.3 portion of the above compound and 5.8 g of chloroacetic anhydride in 35 ml of toluene were reacted as described in Example 1, giving 1.5 g of the desired intermediate, mp 116°–119° C.

EXAMPLE 123

4-(Chloroacetyl-4,5-dihydro-7-(3-methylphenyl)-pyrazolo[1,5-a]pyrimidine-3-carbonitrile This compound is obtained from 7-(3-methylphynyl)-pyrazolo[1,5-a]pyrimidine-3-carbonitrile by the procedure of Example 1.

EXAMPLE 124

4,5-Dihydro-4-[[4-(phenylmethyl)-1-piperazinyl]acetyl]-7-(3-methylphenyl)pyrazolo[1,5-a]pyrimidine By the method of Example 16, N-benzyl piperazine is reacted with 4-(chloroacetyl)-4,5-dihydro-7-methylphenyl)pyrazolo[1,5-a]pyrimidine-3-carbonitrile. The title compound is obtained.

EXAMPLE 125

4-(Chloroacetyl)-4,5-dihydro-7-[3-(trifluoromethyl)-phenyl]pyrazolo[1,5-a]pyrimidine-3-carboxamide A mixture of 2 g of 4-(chloroacetyl)-4,5-dihydro-7-[3-(trifluoromethyl)phenyl]pyrazolo[1,5a]-pyrimidine-3-carbonitrile and 20 ml of concentrated sulfuric acid was stirred at room temperature for 2 hours, then poured into ice water, stirred, and filtered. The product was washed with water and dried giving 2 g of the desired intermediate,. mp 174°–176°

EXAMPLE 126

3-Bromo-4-(chloroacetyl)-4,5-dihydro-7-[3-(trifluoromethyl)phenyl]pyrazolo[1,5-a]pyrimidine The reaction of 10.0 f of 3-bromo-7-[3-(trifluoromethyl)phenyl]pyrazolo[1,5-a]pyrimidine (U.S. Pat. No. 4,178,449) with 4.59 g of sodium cyanoborohydride in 130 ml of acetic acid at 25° for 5 hours gave after workup, 4,4 g of 3-bromo-4,5-dihydro-7-[3-trifluoromethyl)phenyl]pyrazolo[1,5-a]pyrimidine as yellow crystals, mp 101°–103° C.

A 2.5 g portion of the above compound and 3.0 g of chloracetic anhydride in 40 ml of toluene were reacted as described in Example 1, to give 0.8 g of the title compound, m.p. 128°–130° C.

EXAMPLE 127

7-(3-Chlorophenyl)-4,5-dihydro-6-methyl-4-[[4-[[3-(trifluoromethyl)phenyl]methyl]-1-piperazinyl]acetyl]-pyrazolo[1,5-a]pyrimidine-3-carbonitrile The above compound was prepared by the reaction of 4-(3-trifluoromethyl)phenylmethylpiperazine with the compound of Example 12 by the procedure of Example 16, mp 133°–135° C.

EXAMPLE 128

4,5-Dihydro-4-[[4-[(3-trifluoromethylphenyl)methyl]-1-piperazinyl]acetyl]-7-[3-(trifluoromethyl)phenyl]-pyrazolo[1,5-a]pyrimidine-3-carbonitrile The above compound was prepared by the reaction of 4-(3-trifluoromethyl)phenylmethylpiperazine with the compound of Example 1 by the method of Example 16, mp 178°–180° C.

EXAMPLE 129

7-(2,5-Dichlorophenyl)-4,5-dihydro-4-[(4-phenyl-1-piperidinyl)acetyl]pyrazolo[1,5-a]pyrimidine-3-carbonitrile The above compound was prepared by the reaction of 4-phenylpiperidine with the compound of Example 9 by the method of Example 16, mp 199°–200° C.

EXAMPLE 130

7-(2,5-Dichlorophenyl)-4,5-dihydro-4-[[4-(phenylmethyl)-1-piperidinyl]acetyl]pyrazolo[1,5-a]pyrimidine-3-carbonitrile The above compound was prepared by the reaction of 4-benzylpiperidine with the compound of Example 9 by the procedure of Example 16, mp 157°–158° C.

EXAMPLE 131

7-(3-Chlorophenyl)-4-[[4-[(3-Chlorophenyl)methyl-1-piperazinyl]acetyl]4,5-dihydro-6-methylpyrazolo[1,5-a]pyrimidine-3-carbonitrile, dihydrochloride The above compound was prepared by the reaction of 4-(3-chlorophenyl)methylpiperazine with the compound of Example 12 by the procedure of Examples 16 then 77, mp 208°–210° C.

EXAMPLE 132

4,5-Dihydro-4-[[4-(2-phenylethyl)-1-piperazinyl)acetyl]-7-[3-(trifluoromethyl)phenyl]pyrazolo[1,5-a]pyrimidine-3-carbonitrile, dihydrochloride The above compound was prepared by the reaction of 4-(2-phenylethyl)piperazine with the compound of Example 1 by the methods of Examples 16 then 77, mp 235°–237° C.

EXAMPLE 133

7-(4-Chlorophenyl)-4-[[4-[(3-chlorophenyl)methyl]-1-piperazinyl]acetyl]-4,5-dihydro-6-methylpyrazolo[1,5-a]pyrimidine-3-carbonitrile. dihydrochloride The above compound was prepared by the reaction of 4-(3-chlorophenyl)methylpiperazine with the compound of Example 14 by the methods of Examples 16 then 77, mp 250° C. (with sintering).

EXAMPLE 134

4-[[4-[Bis(4-fluorophenyl)methyl-1-piperazinyl]acetyl]-4,5-dihydro-7-[3-(trifluoromethyl)phenyl]pyrazolo[1,5-a]pyrimidine-3-carbonitrile. dihydrochloride The above compound was prepared by the reaction of 4-bis(4-fluorophenyl)methylpipeazine with the compound of Example 1 by the procedures of Examples 15 then 77, mp 255°–258° C.

EXAMPLE 135

4,5-Dihydro-6-methyl-4-[[4-(phenylmethyl)-1-piperazinyl]acetyl]-7-[3-(trifluoromethyl)phenyl]-pyrazolo[1,5-a]pyrimidine-3-carbonitrile, dihydrochloride The above compound was prepared by the reaction of N-benzylpipeazine with the compound of Example 10 by the methods of Example 16 then 77, mp 204°≧2-6° C.

EXAMPLE 136

N-[3-[4-(Chloroacetyl)-(3-cyano-4,5-dihydropyrazolo[1,5-a]pyrimidin-7-yl]phenyl]acetamide A mixture of 7.0 g of 3'-actamido-3-(N,N-dimethylamino)acrylophenone and 3.3 g. of 3-amino-4-cyanopyrazole in 100 ml of acetic acid was heated at reflux for 8 hours. Crystals that formed on cooling were filtered and dried to give 7.4 g. of N-[3-(3-cyanopyrazolo[1,5-a]pyrimidin-7-yl)phenyl[acetamide, m.p. 254°-256° C. This was reacted with 14.8 g of sodium cyanoborohydride in 50 ml of acetic acid to give 3.0 g of N-[3-(3-cyano-4,5-dihydropyrazolo[1,5-a]pyrimidin-7-yl)phenyl]acetamide, m.p. 251°-254° C. This is reacted with chloroacetic anhydride and sodium carbonate in toluene as in Example 3 to give the title compound.

EXAMPLE 137

N-[3-[4-(Chloroacetyl)-(3-cyano-4.5-dihydropyrazolo[1,5-a]pyrimidinyl)phenyl]-N-methylacetamide To 33.0 g of 3'-acetamido-3-dimethylaminoacrylophenone in 170 ml of dimethylformamide was added 6.8 g of 60% sodium hydride followed by 40 g of methyl iodide to give, after workup, 10.5 g of 3'-(N-methylacetamido)-3-(N,N-dimethylamino)acrylophenone, m.p. 129°-131° C. This was reacted with 4.60 g of 3-amino-4-cyanopyrazole in 150 ml of acetic acid at reflux for 16 hrs. to give 7.4 g of N-[3-(3-cyanopyrazolo[1,5a]pyrimidinyl)phenyl]-methylactamide as yellow crystals, m.p. 201°-203° C. This was reacted with sodium cyanoborohydride to give N-[3-(3-cyano-4,5-dihydropyrazolo[1,5-a]pyrimidin-7-yl)phenyl]-N-methylacetamide as yellow crystals, m.p. 114°-120° C. This is reacted with chloroacetic anhydride and sodium carbonate in toluene as in Example 3 to give the title compound.

EXAMPLE 138

N-[3-[[4-(Phenylmethyl)-1-piperazinyl]acetyl(3-cyano-4,5-dihydropyrazolo[1,5-a]pyrimidin-7-yl]phenyl]acetamide The above compound is obtained from N-benzyl piperazine and N-[3-[4-(chloroacetyl)-(3-cyano-4,5-dihydropyrazolo[1,5-a]pyrimidin-7-yl)phenyl]acetamide by the method of Example 16.

EXAMPLE 139

N-[3-[[4-[Phenylmethyl)-1-pipeazinyl]acetyl(3-cyano-4,5-dihydropyrazolo[1,5-a]pyrimidin7-yl)]phenyl]-N-methylacetamide The above compound is obtained from N-benzyl piperazine and N-[3-[4-(chloroacetyl)(3-cyano-4,5-dihydropyrazolo[1,5-a]pyrimidin-7yl)phenyl]-N-methylacetamide by the method of Example 16.

EXAMPLE 140

4,5-Dihydro-6-ethyl-4[[4-(phenylmethyl)-1-piperazinyl]acetyl]7-[3-(trifluoromethyl)phenyl]pyrazolo[1,5-a]pyrimidine-3-carbonitrile A mixture of 3.3 g of 4-(chloroacetyl)4,5-dihydro-6-ethyl-7-[3-(trifluoromethyl)phenyl]pyrazolo[1,5-a]pyrimidine-3-carbonitrile, 1.6 ml of 1-benzylpiperazine and 1 g. of sodium carbonate in 110 ml of toluene was stirred and refluxed for 18 hours. The mixture was treated with 10 ml of 5N sodium hydroxide and the organic phase was separated, dried over sodium sulfate and evaporated to give a dark oil. This was dissolved in ether and combined with ethanolic hydrogen chloride to give a white solid and this solid was recrystallized from acetonitrile to give 3.4 g to the title compound, m.p. 184°-186° C.

The reactants were prepared as follows. Using the method of Example 2, 4,5-dihydro-6-ethyl-7 -[3-(trifluoromethyl)phenyl]pyrazolo[1,5-a]pyrimidine-3-carbonitrile was reacted with chloroacetyl chloride to give 4-(chloroacetyl)-4,5-dihydro-6-ethyl-7-[3-(trifluoromethyl)phenyl]pyrazolo[1,5-a]pyrimidine-3-carbonitrile, m.p. 150°-152° C.

By the method of Example 1,6-ethyl-7-[3-(trifluoromethyl)phenyl]pyrazolo[1,5-a]pyrimidine-3-carbonitrile was reacted with sodium cyanoborohydride in acetic acid to give the 4,5-dihydro derivative, m.p. 185°-187° C.

A mixture of 4.0 go of 3-dimethylamino-2-ethyl-3'-trifluoromethylacrylophenone and 1.5 g of 3-amino-4-cyanopyrazole in 75 ml of glacial acetic acid was refluxed for two hours to give 6-ethyl-7-[3-(trifluoromethyl)phenyl]pyrazolo[1,5-a]]pyrimidine-3-carbonitrile, m.p. 135°-137° C.

The reaction of 3'-trifluoromethylbutyrophenone and dimethylformamide dimethylacetal gave the above acrylophenon, as a liquid, b.p. 90°-95° C. (0.05 mm Hg).

To 30.0 g of 2-morpholinyl-3'-trifluoromethylphenylacetonitrile in 250 ml of N,N-dimethylformamide at 10° C. was added 5.2 g of 50% sodium hydride-mineral oil and to this was added 18.7 g of iodopropane. The reaction mixture was stirred for 18 hours and then was poured into water and the resultant oil was collected to give 33.2 g of 2-morpholinyl-2-propyl-3'-trifluoromethylphenylacetonitrile. This was hydrolyzed by heating in 70% acetic acid, followed by neutralization with sodium hydroxide to give 15.3 g of 3'-trifluoromethylbutyrophenone as a yellow liquid, b.p. 60°-65° C. (0.05 mm Hg).

EXAMPLE 141

4,5-Dihydro-4-[[4-(1-phenylethyl)-1-piperazinyl]acetyl7-[3-(trifluoromethyl)phenyl]pyrazolo[1,5-a]pyrimidine3-carbonitrile To a mixture of 6 g of 4,5-dihydro-4-(1-piperazinylacetyl)-7-[3-trifluoromethyl)phenyl]-pyrazolo[1,5-a]pyrimidine-3-carbonitrile and 2.2 g of diisopropylethylamine in 140 ml of dry dimethylformamide under nitrogen was added with stirring 3.2 g of 1-bromoethyl benzene. This mixture was stirred under reflux for 5 hours, then at room temperature for 48 hours and the solvent evaporated. The residual oil was dissolved in chloroform and shaken with 50 ml of 1N sodium hydroxide. The chloroform layer was washed with saturated salt solution, dried, filtered and concentrated. The residual oil was redissolved in 25 ml of chloroform, filtered through a column of hydrous magnesium silicate and washed with 300 ml of chloroform. The combined filtrate and wash was concentrated and the solid washed with ether and filtered. The crystalline solid was heated to solution in 25 ml of acetonitrile and filtered. The filtrate was cooled and the resulting crystals collected washed with ether and dried giving 1.6 g of the desired product, mp 177°–179° C.

EXAMPLE 142

7-(4-Chlorophenyl)-4,5-dihydro-6-methyl-4-[[4-[[3-(trifluoromethyl)phenyl]methyl-1-piperazinyl]acetyl]-pyrazolo[1,5-a]pyrimidine-3-carbonitrile, dihydrochloride An ether solution of 7-(4-chlorophenyl)-4,5-dihydro-6-methyl-4-[[4-[[3-(trifluoromethyl)phenyl]methyl]-1-piperazinyl]acetyl]pyrazolo[1,5-a]pyrimidine3-carbonitrile was acidified with ethanolic hydrochloric acid. The resulting solid was collected, washed with ether and dried. This solid was recrystallized from ethanol, giving 2.2 g of the desired product, mp 201°–203° C.

EXAMPLE 143

7-(3-Chlorophenyl)-4,5-dihydro-4-[[4-[(3-methoxyphenyl)methyl]-1-piperazinyl]acetyl]-6-methyl-pyrazolo[1,5-a]pyrimidine-3-carbonitrile, dihydrochloride A mixture of 2.7 g of 4-(chloroacetyl)-7-(3-chlorophenyl)-4,5-dihydro-6-methylpyrazolo[1,5-a]pyrimidine-3-carbonitrile, 920 mg of sodium carbonate and 1.7 g of 3-methoxybenzyl piperazine in 100 ml of toluene was stirred for 18 hours, then treated with 25 ml of 1N sodium hydroxide and shaken. The layers were separated and the alkaline layer extracted with chloroform. This extract and the toluene layer were combined, washed with water dried, filtered and concentrated. The residual oil was triturated in ether then concentrated and dissolved with heating in 25 ml of ethanol. A 10 ml portion of 2.44 N ethanolic hydrochloric acid and an excess of ether were added and the solid was collected. This solid was crystallized from hot acetonitrile giving 1.4 g of the desired product, mp 195°–197° C.

EXAMPLE 144

4,5-Dihydro-4-[[4-(2-phenylethyl)-1-piperazinyl]acetyl-7-[3-(trifluoromethyl)phenyl]pyrazolo[1,5-a]pyrimidine-3-carbonitrile, dihydrochloride A 1 g portion of 4,5-dihydro-4-[[4-(2-phenylethyl)-1-Piperazinyl]acetyl]-7-[3-(trifluoromethyl)phenyl]-pyrazolo[1,5-a]pyrimidine-3-carbonitrile was heated to boiling in 50 ml of ethanol, then cooled and acidified with 3 ml of 2.44 N ethanolic hydrochloric acid. An excess of ether was added, the solid collected, washed with ether and dried, giving 900 mg of the desired product, mp 235°–237° C.

EXAMPLE 145

4,5-Dihydro-7-[3-(trifluoromethyl)phenyl-4-[[4-[[3-(trifluoromethyl)phenyl]methyl]-1-piperazinyl]acetyl]-pyrazolo[1,5-a[pyrimidine-3-carbonitrile, dihydrochloride A hexane solution of 4.6 g of 4,5-dihydro-7-[3-(trifluoromethyl)phenyl]-4-[[4-[[3-(trifluoromethyl)-phenyl]methyl]-1-piperazinyl]acetyl]pyrazolo]1,5-a]pyrimidine-3-carbonitrile was acidified with 3 ml of 2.44 N ethanolic hydrochloric acid. Excess ether was added and the solid collected washed with ether and dried. This solid was crystallized from acetonitrile/ether, giving 200 mg of the desired product, mp 204°–206° C.

EXAMPLE 146

4,5-Dihydro-4-[[4-[(2-phenyl-2H-1,2,3-triazol-4-yl)methyl]-1-piperazinyl]acetyl]-7-[3-trifluoromethyl)-phenyl]pyrazolo[1,5-a]pyrimidine-3-carbonitrile A reaction mixture comprising 3.4 g of 1-[(2-phenyl2H-1,2,3-triazol-4yl)methyl]piperazine, 4.4 g of 4-(chloroacetyl)-4,5-dihydro-7-[3-(trifluoromethyl)-phenyl]pyrazolo[1,5-a]pyrimidine-3-carbonitrile and 1.6 g of sodium carbonate in 165 ml of toluene was heated for 18 hours and then shaken with 25 ml of 1N sodium hydroxide. The aqueous-alkaline layer was separated and extracted with chloroform. This extract and the toluene layer were combined, shaken with saturated salt solution, dried, filtered and concentrated. The residue was triturated with ether, filtered and dried. The solid was recrystallized from acetonitrile giving 4 g of the desired product, mp 141°–143° C.

EXAMPLE 147

4,5-Dihydro-7phenyl-4-[[4-(phenylmethyl)-1-piperazinyl]acetyl]pyrazolo[1,5-a]pyrimidine-3-carbonitrile A mixture of 3.8 g of 4-(chloroacetyl)-4,5-dihydro-7-phenylpyrazolo[1,5-a]pyrimidine-3-carbonitrile, 2.5 ml of N-benzylpiperazine and 1.6 g of sodium carbonate in 165 ml of toluene was reacted as described in Example 146, giving 4 g of the desired product, mp 156–158.

EXAMPLE 148

4,5-Dihydro-4-[[4-[(3-methoxyphneyl)methyl]-1-piperazinyl]acetyl]-7-phenylpyrazolo[1,5-a]-pyrimidine-3-carbonitrile A mixture of 3.8 g of 4-(chloroacetyl)-4,5-dihydro-7-phenylpyrazolo[1,5-a]pyrimidine-3-carbonitrile, 2.9 g of 3-methoxybenzyl piperazine and 1.6 g of sodium carbonate in 165 ml of toluene was reacted as described in Example 146. The product was recrystallized from isopropanol, giving 1.5 g of the desired product, mp 98°–100° C.

EXAMPLE 149

4,5-Dihydro-7-(3-methylphenyl)-4-[[4-(phenylmethyl)-1-piperazinyl]acetyl]pyrazolo[1,5-a]pyrimidine-3-carbonitrile, hydrochloride A mixture of 3.3 g of 4-(chloroacetyl)-4,5-dihydro-7-(3-methylphenyl)pyrazolo[1,5-a]pyrimidine-3-carbontrile, 1.9 ml of 1-benzylpiperazine and 1.3 g of sodium carbonate in 130 ml of toluene was reacted as described in Example 146, giving 2.7 g of the neutral base form of the product. A 1.0 g portion of this base was warmed to solution in 20 ml of ethanol and then treated with 3 ml of 2.44N ethanolic hydrochloric acid and an excess of ether, giving 900 mg of the desired product, mp 205°–207° C.

EXAMPLE 150

4,5-Dihydro-4-[[4-[(3-methoxyphenyl)methyl]-1-piperazinyl]acetyl]-7-phenylpyrazolo[1,5-a]pyrimidine-3-carbonitrile, dihydrochloride A 1.3 g portion of 4,5-dihydro-4-[[4-[(3-methoxyphenyl)methyl]-1-piperazinyl]acetyl]-7-phenylpyrazolo[1,5-a]pyrimidine-3-carbonitrile was reacted as described in Example 142, giving 1.2 g of the desired product, mp 222°-225° C.

EXAMPLE 151

4,5-Dihydro-7-[3-(trifluoromethyl)phenyl]-4-[[4-[[2-trifluoromethyl)phenyl]methyl]-1-piperazinyl]acetyl]-pyrazolo[1,5-a]pyrimidine-3-carbonitrile A mixture of 7.4 g of 4-(chloroacetyl)-4,5-dihydro-7-[3-(trifluoromethyl)phenyl]pyrazolo[1,5-a]pyrimidine-3-carbonitrile, 5.4 g of 2-trifluoromethylbenzyl piperazine and 2.4 g of sodium carbonate in 260 ml of toluene was reacted as described in Example 146, giving 6.1 g of the desired product, mp 169°-171° C.

EXAMPLE 152

4,5-Dihydro-7-[3-(trifluoromethyl)phenyl]-4-[[4-[[2-(trifluoromethyl)phenyl]methyl]-1-piperazinyl]acetyl]-pyrazolo[1,5-]pyrimidine-3-carbonitrile dihydrochloride 4,5-Dihydro-7-[3-(trifluoromethyl)phenyl]-4-[[4-[[2-(trifluoromethyl)phenyl]methyl]-1-piperazinyl]acetyl]-pyrazolo[1,5-a]pyrimidine-3-carbonitrile was reacted as described in Example 142, giving 2.3 g of the desired product, mp 220°-222° C.

EXAMPLE 153

4-[[4-(4-Fluorophenyl)-1-piperazinyl]acetyl]4,5-dihydro-7-[3-(trifluoromethyl)phenyl]pyrazolo-[1,5-a]pyrimidine-3-carbonitrile, monohydrochloride A 6.6 g portion of 4-[[4-(4-fluorophenyl)-1-piperazinyl]acetyl]-4,5-dihydro-7-[3-(trifluoromethyl)-phenyl]pyrazolo[1,5-a]pyrimidine-3-carbonitrile was heated to solution in 100 ml of ethyl acetate, then cooled and acidified with 25 ml of 2.44 N ethanolic hydrochloric acid. Ether was added, the solid collected, heated to boiling in 500 ml of ethanol, then cooled and the crystalline salt collected, giving 5.7 g of the desired product, mp 242°-244° C.

EXAMPLE 154

3-Bromo-4,5-dihydro-4-[[4-(phenylmethyl)-1-piperazinyl]acetyl]-7-[3-(trifluoromethyl)phenyl]-pyrazolo[1,5-a]pyrimidine, dihydrochloride A 1.1 g portion of 3-bromo-4,5-dihydro-4-[[4-(phenylmethyl)-1-piperazinyl]acetyl]-7-[3-(trifluoromethyl)phenyl]pyrazolo[1,5-a]pyrimidine was reacted as described in Example 142, giving 1.1 g of the desired product, mp 224°-226° C.

EXAMPLE 155

3-Chloro-4,5-dihydro-4-[[4-(phenylmethyl-1-piperazinyl]acetyl]-7-[3-trifluoromethyl)phenyl]-pyrazolo[1,5-a]pyrimidine, dihydrochloride A mixture of 2.8 g of 3-chloro-4-chloroacetyl-7-[3-(trifluoromethyl)phenyl]pyrazolodihydropyrimidine, 1.3 g of 1-benzylpiperazine, 1.6 g of triethylamine and 100 ml of tetrahydrofuran was stirred under reflux for 18 hours, then cooled and filtered. The filtrate was distilled under vacuum. The crude product was dissolved in 75 ml of chloroform, washed with water, dried, filtered and concentrated. The residual oil was triturated in hexane:ether (3:1(. The crystals were collected, washed with hexane and dried, giving 2.2 g of the product as the free base, mp 108°-110° C. A 1.2 g portion of this base was treated with 4 ml of 2.44N ethanolic hydrochloric acid and an excess of ether. The solid was collected, washed with ether and dried, then recrystallized from acetonitrile/ether, giving 760 mg of the desired dihydrochloride salt. mp 222°-224° C.

EXAMPLE 156

4-[[4-[(2-Fluorophenyl)methyl]-1-piperazinyl]acetyl]-4,5-dihydro-7-[3-(trifluoromethyl)phenyl]pyrazolo[1,5-a]pyrimidine-3-carbonitrile A mixture of 6.3 g of 4-(chloroacetyl)-4,5-dihydro-7-[3-(trifluoromethyl)phenyl]pyrazolo[1,5-a]pyrimidine-3-carbonitrile, 3.7 of 2-fluorobenzyl piperazine and 4.1 g of triethylamine in 250 ml of tetrahydrofuran was stirred under reflux for 18 hours, then cooled and diluted with 500 ml of water. The resulting solid was collected, washed with water, dried, then heated to solution in 200 ml of ethyl acetate, filtered and refrigerated. The resulting solid was collected, washed with hexane and dried, giving 7.1 g of the desired product, mp 188°-190° C.

EXAMPLE 157

7-(3-Chlorophenyl)-4-[[4-[(2-fluorophenyl)methyl]-1-piperazinyl]acetyl]-4,5-dihydro-6-methylpyrazolo[1,5-a]pyrimidine-3-carbonitrile, dihydrochloride A mixture of 4.8 g of 4-(chloroacetyl)-7-(3-chlorophenyl)-4,5-dihydro-6-methylpyrazolo[1,5-a]pyrimidine-3-carbonitrile, 3 g of 2-fluorobenzylpiperazine and 3.4 g of triethylamine in 200 ml of tetrahydrofuran was stirred under reflux for 18 hours, then cooled and treated with 750 ml of water. The resulting oil was extracted into dichloromethane, dried filtered and concentrated to a red-orange viscous oil. This oil was dissolved in 50 ml of acetonitrile and an excess of ether and 18 ml of 3.74N ethanolic hydrochloric acid added. After standing overnight the solid was collected, washed with ethanol and ether, dried and recrystallized from ethanol, giving 4.5 g of the desired product, mp 192°-194° C.

EXAMPLE 158

4-[2-[3-Cyano-7-[3-(trifluoromethyl)phenyl]-pyrazolo[1,5-a]pyrimidin-4(5H)-yl]-2-oxoethyl]-1-piperazinecarboxylic acid, phenylmethyl ester A mixture of 6.3 g of 4-(chloroacetyl)-4,5-dihydro-7-[3-(trifluoromethyl)phenyl]pyrazolo[1,5-a]pyrimidine-3-carbonitrile, 4.2 g of 1-piperazinecarboxylic acid, phenylmethyl ester and 4.1 g of triethylamine in 250 ml of tetrahydrofuran was stirred under reflux for 18 hours, then cooled and filtered. The filtrate was evaporated, the residue taken up in chloroform, washed with water, dried, filtered and concentrated. The residual oil was triturated three times with ether:hexane (1:1), then with hexane. The solid was collected, washed with hexane and dried. The solid was heated to solution in 25 ml of ethyl acetate, filtered, diluted with 25 ml of hexane and cooled, giving 4.6 g of the desired product, mp 113°-115° C.

EXAMPLE 159

4-[2-[3-Cyano-7-[3-(trifluoromethyl)phenyl]-pyrazolo[1,5-a]pyrimidin-4(5H)-yl)-2-oxoethyl]-1-piperazinecarboxylic acid, phenylmethyl ester monohydrochloride A 4.6 g portion of 4-[2-[3-cyano-7-[3-(trifluoromethyl)phenyl]pyrazolo[1,5-a]pyrimidin-4(5H)-yl]2-oxoethyl-1-piperazinecarboxylic acid, phenylmethyl ester was reacted as described in Example 142, giving the desired product, mp 225°–227° C.

EXAMPLE 160

4,5-Dihydro-6-methyl-70[3-(trifluoromethyl)phenyl]-4-[[4-[[3-(trifluoromethyl)phenyl]methyl]-1-piperazinyl]acetyl]pyrazolo[1,5-a]pyrimidine-3-dihydrochloride An 880 mg portion of 4,5-dihydro-6-methyl-7-[3-(trifluoromethyl)phenyl]-4-[[4-[[3-(trifluoromethyl)phenylmethyl]-1-piperazinyl]acetyl]pyrazolo[1,5-a]pyrimidine-3-carbonitrile was reacted as described in Example 142, giving the desired compound, mp 184°–186° C.

EXAMPLE 161

4,5-Dihydro-6-ethyl-4-[[4-(phenylmethyl)-1-piperazinyl]acetyl]-7-[3-(trifluoromethyl)phenyl]-pyrazolo[1,5-a]pyrimidine-3-carbonitrile A mixture of 3.8 g of 4-chloroacetyl-4,5-dihydro6-ethyl-&-[3-(trifluoromethyl)phenyl]pyrazolo[1,5-a]pyrimidine-3-carbonitrile, 1.8 ml of 1-benzyl piperazine and 1.1 g of sodium carbonate in 128 ml of toluene was reacted as described in Example 146, giving 3.7 g of the desired product, mp 97°–99° C.

EXAMPLE 162

4,5-Dihydro-4-[[4-(4-methoxybenzyl)-1-piperazinyl]acetyl]-7-[3-(trifluoromethyl)phenyl]pyrazolo[1,5-a]pyrimidine-3-carbonitrile To a stirred mixture of 3 g of 4,5-dihydro-4-(1-piperazinylacetyl)-7-[3-(trifluoromethyl)phenyl]-pyrazolo[1,5-a]pyrimidine-3-carbonitrile and 1.7 g of "Proton Sponge" in 50 ml of tetrahydrofuran was added 1.4 g of 4-anisoyl chloride. The mixture was stirred under reflux for 18 hours, then cooled and filtered. The filtrate was concentrated and the residue dissolved in chloroform, washed with water, dried, filtered and concentrated. The residual oil was triturated several times with ether, then with hexane and the solid collected and dried. This solid was crystallized from ethyl acetate/hexane, giving 1.2 g of the desired product, mp 151°–153° C.

EXAMPLE 163

4,5-Dihydro-4-[[4-(4-methoxybenzoyl)-1-piperazinyl]acetyl]-7-[3-(trifluoromethyl)phenyl]pyrazolo[1,5-a]pyrimidine-3-carbonitrile, monohydrochloride 4,5-Dihydro-4-[[4-(4-methoxybenzoyl)-1piperazinyl]acetyl]-7-[3-(trifluoromethyl)phenyl]-pyrazolo[1,5-a]pyrimidine-3-carbonitrile was reacted as described in Example 142, giving 230 g of the desired product, mp 241°–243° C.

What is claimed is:

1. A compound of the formula:

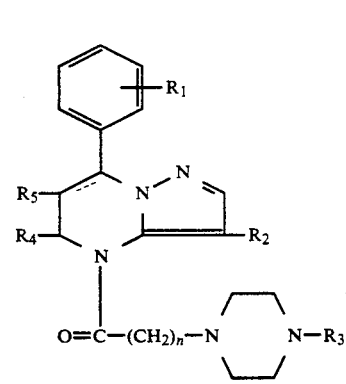

wherein n is an integer from 1 to 4 inclusive; $R_1$ represents a mono- or disubstituent of hydrogen, lower alkyl($C_1$–$C_3$), lower alkoxy($C_1$–$C_3$), halogen, nitro or trifluoromethyl; $R_2$ is cyano, carboxamido, ethoxycarbonyl or halogen; $R_3$ is hydrogen, straight or branched chain lower alkyl($C_1$–$C_3$), alkyl($C_2$–$C_3$), cycloalkyl ($C_3$–$C_6$), hydroxyalkyl($C_1$–$C_3$), dimethylaminoalkyl($C_1$–$C_3$), ethoxycarbonyl, alkyl($C_1$–$C_{13}$)carbonyl, 1-[2-(methylethyl)amino-2-oxoethyl], cyclohexylethyl, phenyl, mono- or disubstituted phenyl (wherein the phenyl substituent is halogen, trifluoromethyl, lower alkyl($C_1$–$C_3$) or lower alkoxy($C_1$–$C_3$)), benzoyl, 4-methoxybenzoyl, straight or branched chain alkyl($C_2$–$C_3$)phenyl, (4-chlorophenyl)phenylmethyl, 1,3-benzodioxol-5-ylmethyl, 1,3-benzodioxol-5yl, 2-furanylcarbonyl, 2-pyrimidinyl, 2-pyridinyl, 4-morpholinyl-2-oxoethyl, 1-pyrrolidinyl-2-oxoethyl, bis(4-fluorophenyl)methyl, phenylcarboxamido, mono- and disubstituted phenylcarboximido (wherein the phenyl substituents is halogen, trifluoromethyl or lower alkyl ($C_1$–$C_3$)), adamantanoyl, 3-phenoxypropyl, (2-oxo-1-pyrrolidinyl)-2-butynyl, phenylmethoxycarbonyl, or (2-phenyl-2H-1,2,3-triazol-4yl)methyl; $R_4$ and $R_5$ are independently hydrogen or lower alkyl ($C_1$–$C_3$), the dotted line between positions 6 and 7 of the pyrimidine ring represents the presence or absence of a double bond; and the pharmacologically-acceptable salts thereof.

2. A compound according to claim 1, 7-(2,5-Dichlorophenyl)-4-[[4-(2,5-dimethylphenyl)-1-piperazinyl]-acetyl]-4,5-dihydropyrazolo[1,5-a]-pyrimidine-3-carbonitrile.

3. A compound according to claim 1, 4-[(4-Benzoyl-1-piperazinyl)acetyl]-4,5-dihydro-7-[3-(trifluoromethyl)phenyl]pyrazolo[1,5-a]pyrimidine-3-carbonitrile.

4. A compound according to claim 1, 7-(2,5-Dichlorophenyl)-4,5-dihydro-4-[4-phenyl-1-piperazinyl) acetyl]pyrazolo[1,5-a]pyrimidine-3-carbonitrile.

5. A compound according to claim 1, 4-[(4-Cyclobutyl-1-piperazinyl]-acetyl]-4,5-dihydro-7-[3-(trifluoromethyl)phenyl]pyrazolo[1,5-a]pyrimidine-3-carbonitrile, dihydrochloride.

6. A compound according to claim 1, 4,5-Dihydro-4-[[4-[(2-phenyl-2H-1,2,3-triazol-4-yl)methyl]-1-piperazinyl]acetyl]7-[3-(trifluoromethyl)phenyl]-pyrazolo[1,5-a]pyrimidine-3-carbonitrile.

7. A compound according to claim 1, 4-[2-[3-Cyano-70[3-(trifluoromethyl)phenyl]pyrazolo[1,5-a]pyrimidin-4(5H)-yl]-2-oxoethyl]-1-piperazinecarboxylic acid, phenylmethylester.

8. A compound 4,5-Dihydro-4-[[4-(2-phenylethyl)-1-piperazinyl]actyl]-7-[3-trifluoromethyl)phenyl]-pyrazolo[1,5-a]pyrimidine-3-carbonitrile.

9. A therapeutic composition of matter in dosage unit form comprising from about 10 mg to about 500 mg per dosage unit of a compound of claim 1, in association with a pharmaceutically acceptable carrier.

10. A method of treating depression in a warm-blooded animal which comprises administering internally to said animal an antidepressant amount of a compound of claim 1.

* * * * *